United States Patent
Correnti et al.

(10) Patent No.: US 10,921,763 B1
(45) Date of Patent: Feb. 16, 2021

(54) BABY MONITORING USING A HOME MONITORING SYSTEM

(71) Applicant: Alarm.com Incorporated, Tysons, VA (US)

(72) Inventors: Matthew Daniel Correnti, Reston, VA (US); Robert Nathan Picardi, Herndon, VA (US)

(73) Assignee: Alarm.com Incorporated, Tysons, VA (US)

( * ) Notice: Subject to any disclaimer, the term of this patent is extended or adjusted under 35 U.S.C. 154(b) by 12 days.

(21) Appl. No.: 16/170,247

(22) Filed: Oct. 25, 2018

Related U.S. Application Data

(60) Provisional application No. 62/576,687, filed on Oct. 25, 2017.

(51) Int. Cl.
| | |
|---|---|
| *G05B 15/02* | (2006.01) |
| *B64C 39/02* | (2006.01) |
| *G05D 1/10* | (2006.01) |
| *G10L 25/48* | (2013.01) |
| *G01J 1/42* | (2006.01) |
| *G01N 33/00* | (2006.01) |
| *H04R 1/02* | (2006.01) |
| *H04N 7/18* | (2006.01) |
| *G06K 9/00* | (2006.01) |
| *G01K 13/00* | (2021.01) |

(52) U.S. Cl.
CPC ............ *G05B 15/02* (2013.01); *B64C 39/024* (2013.01); *G05D 1/101* (2013.01); *B64C 2201/126* (2013.01); *B64C 2201/127* (2013.01); *G01J 1/42* (2013.01); *G01K 13/00* (2013.01); *G01N 33/0027* (2013.01); *G06K 9/00771* (2013.01); *G10L 25/48* (2013.01); *H04N 7/185* (2013.01); *H04R 1/028* (2013.01)

(58) Field of Classification Search
CPC . G05B 15/02; B64C 39/024; B64C 2201/126; B64C 2201/127; G05D 1/101; G01J 1/42; G01K 13/00; G01N 33/0027; G06K 9/00771; G10L 25/48; H04N 7/185; H04R 1/028
See application file for complete search history.

(56) References Cited

U.S. PATENT DOCUMENTS

| | | | |
|---|---|---|---|
| 4,856,130 A | * | 8/1989 | Berkovich ............... A47D 9/02 5/109 |
| 6,054,926 A | | 4/2000 | Deleo |
| 6,462,664 B1 | | 10/2002 | Cuijpers et al. |
| 7,049,968 B2 | | 5/2006 | Fitzgerald et al. |
| 9,117,356 B2 | | 8/2015 | D'Antonio |

(Continued)

*Primary Examiner* — Thomas C Lee
*Assistant Examiner* — Gary Collins
(74) *Attorney, Agent, or Firm* — Fish & Richardson P.C.

(57) ABSTRACT

A monitoring system that is configured to monitor a property is disclosed. In one aspect, the monitoring system includes a sensor that is located in a room of the property and that is configured to generate sensor data. The monitoring system further includes a monitor control unit that is configured to receive the sensor data; based on the sensor data, determine environmental conditions of the room; determine whether the environmental conditions of the room are conducive to a baby sleeping; and, based on determining whether the environmental conditions of the room are conducive to a baby sleeping, perform a monitoring system action.

20 Claims, 5 Drawing Sheets

(56) References Cited

U.S. PATENT DOCUMENTS

| | | |
|---|---|---|
| 9,750,116 B2* | 8/2017 | Witzgall .................. F21S 6/002 |
| 10,558,226 B1* | 2/2020 | Bigdeli ................. G01C 21/206 |
| 2003/0067391 A1 | 4/2003 | Fitzgerald et al. |
| 2003/0122676 A1 | 7/2003 | Cuijpers et al. |
| 2004/0113777 A1* | 6/2004 | Matsuhira ........ G08B 13/19645 340/541 |
| 2006/0103522 A1 | 5/2006 | Spencer |
| 2006/0255936 A1 | 11/2006 | Mathews et al. |
| 2008/0077020 A1* | 3/2008 | Young .................. A61B 5/0205 600/484 |
| 2010/0007486 A1* | 1/2010 | Lu ....................... G06F 19/3418 340/539.15 |
| 2010/0060448 A1 | 3/2010 | Larsen et al. |
| 2010/0099954 A1* | 4/2010 | Dickinson ............ A61B 5/6814 600/300 |
| 2011/0230115 A1 | 9/2011 | Wang et al. |
| 2013/0278419 A1 | 10/2013 | D'Antonio |
| 2014/0161345 A1* | 6/2014 | Djugash .................... G06T 7/73 382/153 |
| 2014/0207280 A1* | 7/2014 | Duffley ................. A47L 9/2857 700/257 |
| 2014/0207281 A1* | 7/2014 | Angle .................. H04L 12/282 700/257 |
| 2015/0038072 A1* | 2/2015 | Cordier .................. A47D 15/00 455/39 |
| 2015/0163412 A1* | 6/2015 | Holley ................... G05B 15/02 348/143 |
| 2015/0288877 A1* | 10/2015 | Glazer ................ H04N 5/2256 348/77 |
| 2016/0015278 A1* | 1/2016 | Campo ................ A61B 5/1128 348/143 |
| 2016/0121074 A1* | 5/2016 | Ashby .................. A61M 21/02 600/28 |
| 2016/0150338 A1* | 5/2016 | Kim ........................ G08B 1/08 381/58 |
| 2016/0158942 A1* | 6/2016 | Augenbraun .......... B25J 13/085 700/253 |
| 2016/0183695 A1* | 6/2016 | Veron ..................... A47D 9/00 340/573.1 |
| 2016/0229534 A1* | 8/2016 | Hutson .................. B64C 27/08 |
| 2016/0261425 A1* | 9/2016 | Horton ............... H04L 12/2816 |
| 2016/0292986 A1* | 10/2016 | Pradeep ................. G16H 50/20 |
| 2017/0048403 A1* | 2/2017 | Baba .................. H04N 1/00251 |
| 2017/0048495 A1* | 2/2017 | Scalisi ............... G06K 9/00771 |
| 2017/0078552 A1* | 3/2017 | Pochon ............... H04N 5/2351 |
| 2017/0205827 A1* | 7/2017 | Rezvani .................. G05D 1/02 |
| 2017/0246739 A1* | 8/2017 | Frisby .................... E05F 1/002 |
| 2017/0334065 A1* | 11/2017 | Liao ........................ B25J 9/161 |
| 2018/0053392 A1* | 2/2018 | White ...................... G06T 7/20 |
| 2018/0095714 A1* | 4/2018 | Taylor .................... G06F 3/165 |
| 2018/0125256 A1* | 5/2018 | Tsern ................ G05B 13/0265 |
| 2018/0235471 A1* | 8/2018 | Jeong ................... A61B 5/1118 |
| 2019/0046109 A1* | 2/2019 | Lewis ................... A61B 5/486 |

* cited by examiner

BABY MONITORING USING A HOME MONITORING SYSTEM

CROSS-REFERENCE TO RELATED APPLICATION

This application claims the benefit of U.S. Provisional Application No. 62/576,687, filed Oct. 25, 2017, which is incorporated by reference.

FIELD

This disclosure generally relates to security systems.

BACKGROUND

Parents often remotely monitor babies and small children to ensure a child's safety, health, and well-being when a parent is not physically present with the child.

SUMMARY

Parents and caregivers often remotely monitor babies and small children to ensure the child's safety, health, and well-being when a caregiver is not physically present with the child. Often, a parent remotely monitors a baby while she sleeps, tracking the baby's sleep patterns, ensuring her safe breathing, or listening for the baby to wake or cry, so that the parent may provide care to the baby if necessary. Remote baby monitoring is conventionally accomplished using dedicated two-terminal systems, where a transmitting terminal is placed in the baby's room and a portable receiving terminal is carried by the parent or caregiver. The portable receiving terminal may provide a real-time video and/or audio feed from the baby's room that allows the parent to watch for movement or listen for sound from the baby.

Many parents equip their residence with a home monitoring system to provide increased home security, environmental awareness, and automated home control. For example, a home monitoring system may include sensors such as cameras and noise detectors to monitor the property. It may include temperature, humidity, or gas sensors to track indoor air quality. The home monitoring system may also integrate controls to automate certain actions within the home, for example, activating a heating, ventilation, and air conditioning (HVAC) unit, turning on a fan, or switching on a lamp. In some cases, the home monitoring system may include drones or other robotic devices to serve as mobile sensors or actuators to monitor the home or perform actions. The home monitoring system may also include an off-site monitoring server which can perform computationally intensive tasks on the collected data, such as analyzing, correlating, and synthesizing data gathered by multiple sensors in the residence.

The present application discloses systems and methods for using a home monitoring system to remotely monitor a baby. In some implementations, the technique may leverage the integrated sensors and controls of the home monitoring system to track a baby's sleep patterns over time, correlate a baby's sleep quality with environmental conditions, and monitor the baby's breathing and environment for unsafe conditions. In some cases, the system may be configured to perform customized actions or automated responses to detected events (e.g., the baby wakes from sleep, the temperature is outside of a preferred range).

Implementations of the disclosed systems and methods may provide one or more of the following advantages over existing remote baby monitoring techniques. A parent may monitor and record a baby's sleep patterns over a period of days, weeks, or months, developing a historical record of sleep trends that can be used to track the baby's development, health, and overall well-being. By simultaneously monitoring the baby's sleep patterns and the condition of the baby's environment (e.g., temperature, humidity, etc.), the parent may determine the baby's preferred environment for sleep and modify the environment to enhance the baby's sleep quality. The monitoring system may notify a parent of conditions in the room that are sub-optimal for the baby's restful sleep, such as a light level too high or a noise level too low. The monitoring system may notify a parent of conditions that present an unsafe environment or increased risk for the baby. For example, the monitoring system may notify a parent when the baby is sleeping on her stomach or when the room temperature is too warm, both factors that can increase the baby's risk of suffering sudden infant death syndrome (SIDS). The monitoring system may be able to notify the parent when the baby is standing upright or climbing, such that she may risk injury by falling out of the crib. The monitoring system may also be configured to detect signs of distress in the baby and automatically alert the parent. By analyzing video data, the monitoring system may be able to determine and track the baby's breathing rate non-invasively, alerting parents to any detected abnormalities (e.g. intermittent breathing, low breathing rate, ceased breathing) and providing the parents increased peace-of-mind when they are not present with the child. The monitoring system can send sensor information or analyzed data to the parent's mobile device over a cellular network, enabling the parent to remotely monitor the baby from a location outside of the home (e.g., at work, at a restaurant). The parent can configure the monitoring system to automatically perform actions in response to certain sensed conditions or events. For example, the parent can configure the monitoring system to automatically turn on a noise machine if the system detects that the baby has awoken, or to automatically change the thermostat setting if the system detects that the baby's room temperature is outside of a preferred range. The parent can also configure the system to perform an action according to a schedule or on-demand. For example, the parent can configure the system to turn off a night-light in the baby's room at 8 PM each night, or to turn on a recording of a lullaby when the parent sends a command through his mobile device.

The systems and methods disclosed herein are not limited to monitoring babies. The techniques allow a person to remotely monitor any another individual in the home. For example, a caregiver may wish to remotely monitor a small child, a sick patient, or an elderly family member. The techniques may also be used to monitor pets or other animals when a homeowner is away from the residence. The system may also enable an individual to monitor his own sleep patterns and environment, using the analysis and synthesis capabilities of the monitoring server to evaluate his sleep history and quality. The system can be interconnected to other sensors, such as wearable health monitors, to provide additional information on the correlation of sleep, environmental conditions, and other markers of health for a particular individual.

According to an innovative aspect of the subject matter described in this application, a monitoring system is configured to monitor a property. The monitoring system includes a sensor that is located in a room of the property and that is configured to generate sensor data; and a monitor control unit that is configured to receive the sensor data;

based on the sensor data, determine environmental conditions of the room; determine whether the environmental conditions of the room are conducive to a baby sleeping; and, based on determining whether the environmental conditions of the room are conducive to a baby sleeping, perform a monitoring system action.

This implementation and other implementations may each include one or more of the following optional features. The monitor control unit is configured to determine whether the environmental conditions of the room are conducive to a baby sleeping by determining that the environmental conditions of the room are conducive to a baby sleeping; and perform a monitoring system action by storing data indicating a temperature setting of the room, a position of a window covering in the room, a time of day, and a volume level of a noise machine in the room. The monitoring system of claim 1, wherein the monitor control unit is configured to determine whether the environmental conditions of the room are conducive to a baby sleeping by determining that the environmental conditions of the room are not conducive to a baby sleeping; and perform a monitoring system action by adjusting a temperature setting of the room, adjusting a position of a window covering in the room, and adjusting a volume level of a noise machine in the room. The monitor control unit is configured to adjusting the position of the window covering in the room by instructing a drone to adjust the position of the window covering in the room.

The monitoring system includes a drone includes the noise machine. The monitor control unit is configured to adjust the volume level of the noise machine in the room by instructing the drone to adjust the volume level of the noise machine included in the drone. The sensor is a light sensor that is configured to generate sensor data indicating a light level in the room. The sensor is a microphone that is configured to receive audio data in the room. The sensor is a camera that is configured to generate image data that includes a representation of the room. The sensor is a thermometer that is configured to generate temperature data that indicates a temperature of the room. The sensor is a humidity sensor that is configured to generate humidity data that indicates a humidity level in the room. The sensor is an air quality sensor that is configured to generate air quality data that indicates an air quality level in the room. The sensor is an audio-visual camera that is configured to generate image data that includes a representation of the room and that is configured to receive audio data in the room. The monitor control unit is configured to receive the sensor data by receiving the image data and the audio data; based on the image data, determine that a baby is in the room; based on the audio data, determine that the baby is crying; perform the monitoring system action based on determining that the baby is in the room and that the baby is crying.

The monitor control unit is configured to perform the monitoring system action by instructing a drone to rock a cradle of the baby. The monitor control unit is configured to, based on the image data, determine that a toy of the baby is not within a threshold distance of the baby; and perform the monitoring system action by instructing a drone to retrieve the toy and place the toy in a cradle of the baby. The sensor is an audio-visual camera that is configured to generate image data that includes a representation of the room and that is configured to receive audio data in the room. The monitor control unit is configured to receive the sensor data by receiving the image data and the audio data; based on the image data, determine that a baby is in the room; based on the audio data, determine that the baby is not crying; store data indicating current environmental conditions of the room as environmental conditions of the room that are conducive to a baby sleeping.

According to another innovative aspect of the subject matter described in this application, a method includes the actions of receiving, from a sensor that is located in a room of a property and that is included in a monitoring system that is configured to monitor the property, sensor data; based on the sensor, determining, by the monitoring system, environmental conditions of the room; determining, by the monitoring system, whether the environmental conditions of the room are conducive to a baby sleeping; and, based on determining whether the environmental conditions of the room are conducive to a baby sleeping, performing, by the monitoring system, a monitoring system action.

This implementation and other implementations may each include one or more of the following optional features. The actions further include determining whether the environmental conditions of the room are conducive to a baby sleeping by determining that the environmental conditions of the room are conducive to a baby sleeping; and performing a monitoring system action by storing data indicating a temperature setting of the room, a position of a window covering in the room, a time of day, and a volume level of a noise machine in the room. The actions further include determining whether the environmental conditions of the room are conducive to a baby sleeping by determining that the environmental conditions of the room are not conducive to a baby sleeping; and performing a monitoring system action by adjusting a temperature setting of the room, adjusting a position of a window covering in the room, and adjusting a volume level of a noise machine in the room.

The sensor is a light sensor that is configured to generate sensor data indicating a light level in the room. The sensor is a microphone that is configured to receive audio data in the room. The sensor is a camera that is configured to generate image data that includes a representation of the room. The sensor is a thermometer that is configured to generate temperature data that indicates a temperature of the room. The sensor is a humidity sensor that is configured to generate humidity data that indicates a humidity level in the room. The sensor is an air quality sensor that is configured to generate air quality data that indicates an air quality level in the room. The sensor is an audio-visual camera that is configured to generate image data that includes a representation of the room and that is configured to receive audio data in the room. The actions further include receiving the sensor data by receiving the image data and the audio data; based on the image data, determining that a baby is in the room; based on the audio data, determining that the baby is crying; and performing the monitoring system action based on determining that the baby is in the room and that the baby is crying.

Other implementations include corresponding systems, apparatus, computer-readable storage media, and computer programs configured to implement the actions of the above-noted methods.

The details of one or more implementations are set forth in the accompanying drawings and the description below. Other features and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
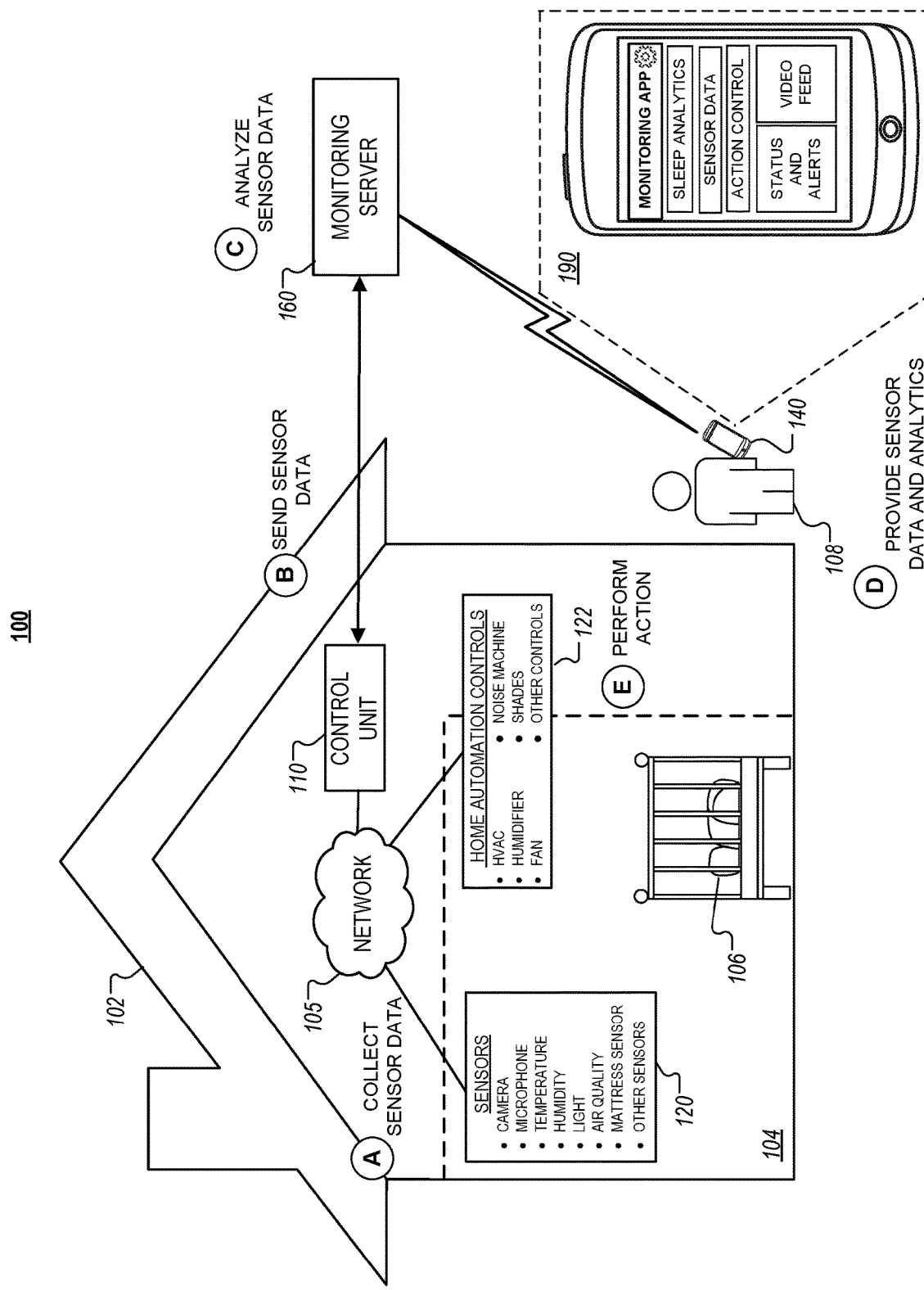
FIG. 1 is a diagram illustrating an example system for remotely monitoring a baby using a home monitoring system.

FIG. 1 is a diagram illustrating an example system 100 for remotely monitoring a baby using a home monitoring system. In system 100, a baby is sleeping in a room of the home, while a parent or caregiver is monitoring the baby remotely. The parent or caregiver may be in another room of the home or may be outside of the home (e.g., at work, at a restaurant, etc.). The system 100 collects data from various sensors in the baby's room or in other parts of the home and sends the data to a monitoring server that is remote from the home. In some implementations, the monitoring server may analyze and synthesize the collected sensor data. For example, the monitoring server may analyze video data to determine when the baby is sleeping restfully and correlate periods of restful sleep with collected environmental data (e.g., temperature, humidity) to determine the environmental conditions most likely to promote the baby's restful sleep. The monitoring server then provides collected sensor data and/or analyzed data to the remote parent's or caregiver's mobile device. Based on predetermined settings or on a command from the remote parent's mobile device, the system 100 can perform an action in the baby's room or another room of the home. For example, if the system 100 senses that the temperature increases above 72° F., the system 100 may activate the HVAC to cool the room. As another example, through his mobile device a parent may command the system 100 to turn on a sound machine in the baby's room. FIG. 1 includes stages (A) through (E), which depict an example process for baby monitoring using system 100.

In FIG. 1, the home monitoring system 100 monitors a home 102. The home 102 may be a single-family dwelling, a townhome, an apartment, or another residence. Within the home 102 is a room 104, e.g., a bedroom or a nursery, in which a baby 106 is present. A parent 108 wants to remotely monitor the baby 106 while he is in another room of the home 102 or while he is outside of the home 102. For example, the parent 108 may want to monitor the baby 106 while he is in the kitchen or in the yard of the home 102. The parent 108 may also want to monitor the baby 106 when he is away from the home and the baby 106 is in the care of another caregiver. For example, the parent 108 may want to remotely monitor the baby 106 while he is at a restaurant and the baby 106 is in the care of a babysitter.

The home monitoring system 100 includes one or more sensors 120 located within the baby's room 104. The sensors 120 may include, for example, cameras, microphones, noise detectors, or other sensors which provide awareness of movement, sound, or other presence in the room 104. The sensors 120 may also include temperature sensors, humidity sensors, light detectors, or air quality sensors that collect information on the environmental conditions in the room 104. For example, the sensors 120 may include volatile organic compound (VOC) or carbon dioxide ($CO_2$) sensors. The sensors 120 may also include safety devices, such as smoke alarms or carbon monoxide (CO) detectors. In some cases, the sensors 120 may include movement sensors, such as a sensor placed onto or integrated into a crib mattress that detects and reports movement of the baby 106. The sensors 120 may collect data continuously (e.g., a continuous video feed) or at repeated intervals (e.g., sensing the air temperature once per minute).

In stage (A), the sensors 120 collect data from the room 104 while the baby 106 is present and send the sensor data to a monitoring system control unit 110. The control unit 110 is located within the home 102 and may receive data from the sensors 120 over a network 105. The network 105 may be wired or wireless and may comprise a local area network (LAN), the internet, WiFi, Bluetooth, or other means for short-range electronic communications. The control unit 110 may also send commands over the network 105 to control the operation of the sensors 120.

For example, in some implementations, the sensors 120 may include a camera and microphone mounted in the room 104 that are directed towards the location of the baby 106. The sensors 120 may also include temperature and humidity sensors located within the room 104 and near to the baby 106. The camera and microphone may monitor the position, movement, and sound of the baby 106, while the temperature and humidity sensors may monitor the environmental conditions of room 104. In stage (A) of FIG. 1, video, audio, temperature, and humidity data collected from the sensors 120 in the room 104 are sent through the network 105 to the control unit 110.

In stage (B), the control unit 110 may send the collected sensor data to a monitoring server 160 that is remote from the home 102. The monitoring server 160 may be maintained and operated by a monitoring company. The control unit 110 communicates with monitoring server 160 over a long-range wired or wireless connection, which could be, for example, a wide area network (WAN), a cellular network, a cable network, a satellite network or another connection for transmitting data. In some examples, the control unit 110 may process the sensor data before sending it to the monitoring server.

In stage (C), the monitoring server 160 may analyze and synthesize sensor or other data received from the control unit 110. In some implementations, the monitoring server 160 may include an analytics engine to analyze video, image, audio, temperature, and/or other sensor data. For example, the monitoring server 160 may analyze video and/or audio data of the baby 106 captured by a camera and microphone within the baby's room 104 to determine the status and quality of the baby's sleep state. In some cases, the monitoring server 160 may analyze the movement and sound of the baby 106 to determine whether the baby 106 is awake or asleep at a given time. The monitoring server 160 may distinguish between different qualities of wakefulness or sleep (e.g., awake and content vs. awake and crying, sleeping restfully vs. sleeping restlessly). In some cases, the monitoring server 160 may associate the quality of the baby's sleep with a ranking or numeric value, where the quality of the baby's sleep can take on a value within a given range (e.g., associate awake with "0," restless sleep with "5", restful sleep with "10"). In some examples, the monitoring server 160 may analyze video data to determine the position and/or orientation of the baby 106. For example, based on the video data, the monitoring server 160 may determine that the baby 106 is laying with her face pressed up against the side of the crib or next to a cloth bumper, conditions that may impede her breathing. The monitoring server 160 may also analyze video data to determine that the baby 106 is sleeping on her back, or is sleeping on her side or stomach. The monitoring server 160 may determine that the baby 106 is sitting or standing in her crib. In some implementations, the monitoring system 160 may analyze video data to detect motion or movement of the baby 106. For example, the monitoring system 160 may determine the breathing rate of the baby 106 by analyzing video data to detect the rhythmic movement of her chest or back. The monitoring system 160 may distinguish when the baby 106 is breathing normally and when she is breathing abnormally (e.g., low breathing rate, intermittent or irregular breathing, ceased breathing). In some cases, the monitoring system 160 may determine that the baby 106 has changed position (e.g., rolled over or sat upright) or is currently moving (e.g., climbing, squirming, etc.). The monitoring server may also use data from other sensors to determine the status of the baby 106, including mattress sensors that detect motion of the baby 106, wearable sensors that detect biometric information from the baby 106, or other sensors.

The monitoring server 160 may store historical sleep data for the baby 106. For example, the monitoring server 160 may store data related to how well the baby 106 slept at different times of day for each day of the previous month. In some cases, the monitoring server 160 may store days, weeks, months or more of sleep data.

In some implementations, the monitoring server 160 may analyze the historical sleep data to determine a baseline sleep pattern for the baby 106. The baseline sleep pattern may, for example, indicate the times during the day or night that the baby 106 is typically awake and content, awake and crying, restlessly sleeping, or restfully sleeping. The monitoring server 160 may determine the baseline sleep pattern by analyzing and synthesizing historical sleep data from multiple days or weeks. To account for changes in the sleep pattern of the baby 106 over time, the monitoring server 160 may determine a rolling baseline sleep pattern, using only the most recent sleep data to calculate the baseline. The monitoring server 160 may use different amounts of historical sleep data to determine the baseline sleep pattern. For example, when the baby 106 is young (e.g., less than six months old), her sleep patterns may change frequently and the monitoring server 160 may use only a few days or a few weeks of sleep data to determine the baseline. When the baby 106 is older (e.g., more than six months old), her sleep patterns may be more stable and the monitoring server 160 may use a few weeks or a few months of sleep data to determine the baseline. In some implementations, the parent 108 can set how many days (and/or which days) of sleep data are used by the monitoring server 160 to determine the baseline sleep pattern.

The monitoring server 160 may perform various analytics on the sleep data to provide the parent 108 information on the sleep patterns of the baby 106. For example, the sleep analytics performed by the monitoring server 160 may reveal that in the last two weeks, on average, the baby 106 slept restfully for eight hours at night if she napped between 1 PM and 2 PM that day, while she slept restfully for only six hours at night if she napped between 3 PM and 4 PM that day. Based on this information, the parent 108 may choose to put the baby 106 down for a nap between 1 PM and 2 PM to increase the likelihood that she sleeps restfully for eight hours at night. The monitoring server 160 may perform analytics on the sleep data from a single period (e.g., one day) or from multiple periods (e.g., across multiple days). The analytic functions performed may include, for example, tallying total hours of restful sleep, tallying when and for how long the baby 106 woke, assigning a score indicating overall quality of sleep, estimating optimal times for restful sleep, calculating sleep markers (e.g., average number of hours of restful sleep each night, average number of times the baby 106 wakes each night), and tracking sleep markers over time and across multiple periods, among other functions. The monitoring server 160 may store the analytic data for future use.

In some implementations, the monitoring server 160 may perform analytics that correlate the sleep data with data recorded by other sensors 120 in the baby's room 104. For example, the monitoring server 160 may correlate the quality of the baby's sleep with the environmental conditions (e.g., temperature, humidity, light level) detected by the sensors 120 in the room 104. The analytics may show, for instance, that the baby 106 tends to sleep restfully when the room temperature is between 68° F. and 72° F. or that the baby 106 tends to wake when the light in the room exceeds a given threshold. The monitoring server 160 may perform analytics that synthesize sleep and other sensor data from a single period (e.g., one day) or from multiple periods (e.g., across multiple days). The analytic functions performed may include, for example, correlating periods of restful or restless sleep with the room temperature, humidity, or light level. The monitoring server 160 may store the analytic data for future use.

In stage (D), the monitoring server 160 provides sensor data and/or analytic data to the parent 108, possibly through a mobile device 140. The mobile device 140 may be, for example, a mobile phone, a smart phone, a tablet, or other portable user device capable of receiving data. In some implementations, the monitoring server 160 may provide data to the mobile device 140 over a network, such as a cellular telephony network, allowing the parent 108 to receive data from the monitoring server 160 when he is away from the home 102.

The monitoring server 160 may provide various data to the remote parent 108 through the mobile device 140. For example, the server may provide data from the sensors 120, such as live or recorded video data from a camera located in room 104 and directed towards the baby 106. The video data can be compressed or uncompressed and may include associated audio data recorded from the room 104. By viewing the video and audio data, the parent 108 can remotely monitor the baby 106 as he would with a conventional two-terminal baby monitoring system. The monitoring server 160 may also provide current or historical data from other sensors 120 to the mobile device 140. For example, the monitoring server 160 may provide the most recent temperature, humidity, and air quality values detected by sensors 120, allowing the parent 108 to remotely monitor the environmental conditions in the baby's room 104. The monitoring server 160 may also provide the parent 108 with analyzed or synthesized data, such as the most recent baseline sleep pattern of the baby 106, the baby's current sleep status (e.g., awake and content, sleeping restlessly), or the baby's current position, orientation, or breathing rate.

The monitoring server 160 may also notify the parent 108 when certain predetermined events occur. In some implementations, monitoring server 160 may alert the parent 108 when the baby 106 appears to be in distress, for example, when her breathing rate has slowed or ceased. The monitoring server 160 may also alert the parent 108 to conditions that may present an increased risk for the baby 106. For example, the monitoring server 160 may alert the parent 108 when it detects that the baby 106 has rolled onto on her stomach, or when the temperature in the room 104 is too high, both of which may increase the baby's risk of suffering sudden infant death syndrome (SIDS). The monitoring server 160 may alert the parent 108 when it determines that the baby 106 is sleeping with her face pressed against the side of the crib, which may impede breathing. The monitoring server 160 may alert the parent 108 when the baby 106 is standing in the crib, or is in an otherwise unsafe position or orientation. The monitoring server 160 may alert the parents when other unsafe conditions are present, for example, when the air quality, as measured by detected VOCs or $CO_2$ levels, drops below a threshold level. In some implementations, the monitoring server 160 may also alert the parent when the conditions within the room 104 have fallen outside of a preferred range (e.g., the temperature is above 72° F., the humidity is above 60%, or the light level is too high). The monitoring server 160 may alert the parent 108 when it detects that the baby 106 has awoken or when a loud noise is detected.

In some implementations, the parent 108 may determine which events the monitoring server 160 will alert them to. For example, the parent 108 may configure the system to provide him alerts when the baby 106 is in distress, but not when the baby 106 is simply awake.

In some implementations, in addition to providing notifications and alerts to the parent 108, the monitoring server 160 may also provide status information, notifications and alerts, as well as analyzed and synthesized data, to the monitoring system control unit 110.

In some implementations, the parent 108 may access the data provided by the monitoring server 160 through a software application 190 on his mobile device 140. The application 190 may provide the parent 108 various options for displaying and interacting with the data provided by the monitoring server 160. One example of a software application 190 is shown in FIG. 1, where the application 190 includes a dashboard with options for viewing sleep analytics for the baby 104, data from sensors 120, status and alerts related to the monitored baby 106, and video data from a camera located in the baby's room 104. Here, the parent 108 may configure the application 190 to customize the data presented (e.g., which data is displayed, the time period displayed, the data scale, and other display properties) according to his preferences. For example, the parent 108 may configure the application such that only video and audio data are displayed, providing conventional baby monitoring functionality. Alternatively, the parent 108 may choose not to view the video data, but to receive a notification when the baby 106 awakes or when the environmental conditions within the room 104 are outside of a preferred range.

The application 190 may also provide the parent 108 with the ability to remotely command actions in the home 102 through the monitoring system control unit 110 (as described in stage (E) below). Here, the parent's mobile device 140 communicates information regarding the commanded action to the monitoring server 160, which relays that information to the control unit 110.

The software application 190 depicted in FIG. 1 is just one of many possible configurations and instantiations, and the features described should not be construed as limiting examples.

In stage (E), in response to sensor data, analyzed data, and/or a command from the parent 108, the monitoring system control unit 110 may perform an action using the home automation controls 122. The home automation controls 122 are connected to the control unit 110 through the network 105 and enable regulation of various systems and devices within the home 102. For example, the automation controls 122 may include an interface to the HVAC system of the home 102, allowing the control unit 110 to change the HVAC thermostat setting or to turn on a ventilation fan. The automation controls 122 may govern the operation of a humidifier, a ceiling fan, or smart window shades within the baby's room 104. The automation controls 122 may also control operation of electronic devices in the baby's room 104 through a smart switch. For example, the automation controls 122 may turn on or off a lamp, a noise machine, or an audio device powered by a smart switch.

In some implementations, the control unit 110 may perform an action through the home automation controls 122 in response to a command sent by the parent 108 through his mobile device 140. Here, the mobile device 140 may communicate the command to the monitoring server 160, which then relays the command to the control unit 110. The parent 108 may indicate the command by, for instance, making a selection in the software application 190 displayed on his mobile device 140. For example, the parent 108 may see in the video data provided by the monitoring server 160 that the baby 106 is awake and crying. By selecting an option in the application 190, the parent 108 may command the control unit 110 to turn on an audio device in room 104 that plays a lullaby to soothe the baby 106 to sleep. As another example, if the monitoring server 160 has notified the parent 108 that the baby 106 has rolled onto her stomach, the parent 108 may activate a vibrator on the bed to encourage the baby 106 to shift to a safer sleeping position.

In some implementations, the control unit 110 may use the home automation controls 122 to automatically perform an action in the home 102 in response to data collected by the sensors 120. For example, through the automation controls 122, the control unit 110 may decrease the thermostat setting on the HVAC system when the temperature in room 104 is detected to drop below 72° F. to maintain the room temperature within the preferred range for the baby's comfort or safety. As another example, the control unit 110 may use the automation controls 122 to turn on a fan in the room 104 when the air quality is detected to drop below a threshold level.

The control unit 110 may also be configured to perform an action through the home automation controls 122 in response to analyzed data provided by the monitoring server 160. For example, when the monitoring server 160 determines that the baby 106 is in an unsafe sleeping position (e.g., on her stomach) or in distress (e.g. slowed breathing rate), the control unit 110 may take automatic action through the home automation controls 122 to rouse the baby 106 (e.g., turning on a sound maker, activating a vibrator on the bed). As another example, the control unit 110 may be configured to turn on a noise machine in the baby's room 104 when the sleep data from the monitoring server 160 indicates that the baby 106 has awoken.

In some systems, the control unit 110 may indicate a status of the home monitoring system (e.g., "unarmed," "armed away," "armed stay"), where that status may be set by the parent 108. For example, the parent 108 may set the status of the monitoring system to "armed stay" when he is present in the home 102, but unavailable (e.g., asleep, engaged in an activity). Alternatively, the parent 108 may set the status of the home monitoring system to "unarmed" when he is present in the home 102 and available. In some implementations, the control unit 110 may determine the action to be performed based, in part, on the status of the home monitoring system. For example, if the temperature in the baby's room 104 is detected to rise above 72° F. and the status of the home monitoring system is "armed stay," the control unit 110 may automatically change the thermostat setting on the HVAC system through the home automation controls 122 because the parent 108 is not available. Alternatively, if the temperature in the baby's room 104 is detected to rise above 72° F. and the status of the home monitoring system is "unarmed," the control unit 110 may not change the thermostat setting, but instead may send a notification to the parent's mobile device 140, allowing the available parent 108 to change the thermostat setting if he desires to.

Figure 2:
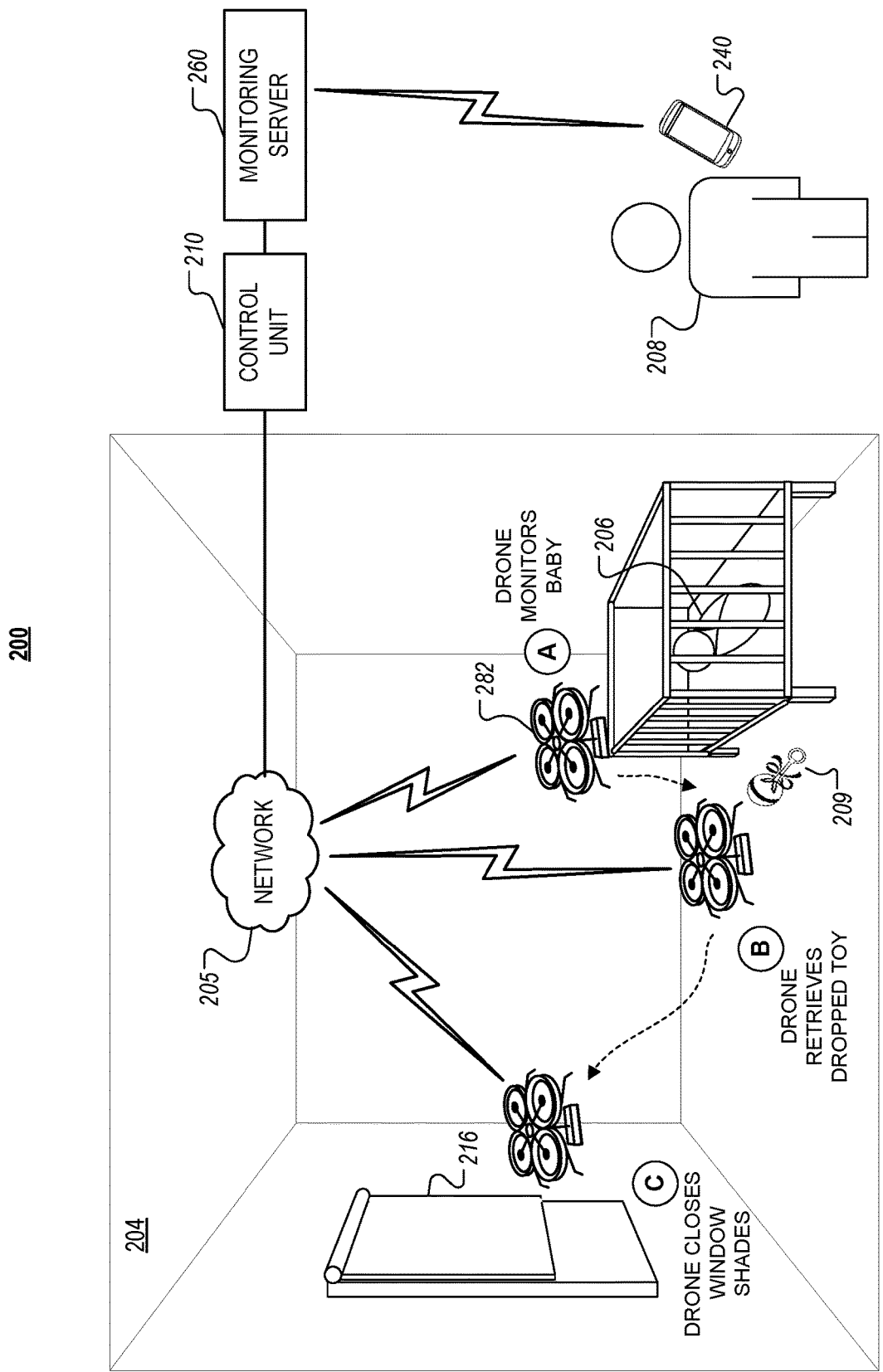
FIG. 2 is a diagram illustrating an example system for remotely monitoring a baby using a home monitoring system that includes a mobile drone.

FIG. 2 is a diagram illustrating an example system 200 for remotely monitoring a baby 206 using a home monitoring system that includes a mobile drone. In example system 200, the home monitoring system 100 of FIG. 1 is supplemented by one or more mobile drones 282 that are present within the baby's room 204. The drone 282 may be equipped with sensors that can monitor the status of the baby 206 as well as the environmental conditions within the room 204. The drone 282 may also move about the room 204 to perform required actions, such as monitoring the baby, retrieving a dropped toy, or closing a window shade. FIG. 2 includes examples (A) through (C) which illustrate possible actions that may be performed by drone 282 as part of the baby monitoring system.

In FIG. 2, the home monitoring system 200 includes a monitoring system control unit 210 within the home that is connected to a short range network 205, also within the home. The network 205 may be wired or wireless and may comprise a local area network (LAN), the internet, WiFi, Bluetooth, or other means for short-range electronic communications. The network 205 may communicate with one or more installed stationary sensors mounted in the room 204 and one or more home automation controls, as described previously in system 100 of FIG. 1.

In addition to the installed stationary sensors and home automation controls, the home monitoring system 200 of FIG. 2 also includes one or more mobile drones 282 that are located within the baby's room 204. The drone 282 is a mobile robotic device that may move about the room 204 under its own locomotion. The drone 282 may move about the floor, or it may have propellers or other features that enable it to fly about the room 204, hover in a given location, or land and balance on an elevated surface. The system 200 depicted in FIG. 2 includes one mobile drone 282, which moves about the room to perform the actions of examples (A), (B), and (C), as needed or directed.

The drone 282 may include onboard sensors, such as a camera, a microphone, a temperature sensor, or an air quality sensor, that move about the room 204 with the drone 282. The drone 282 may include other features for interacting with objects or individuals in its local environment. For example, the drone 282 may include a speaker or a display screen. The drone 282 may have mechanical features or attachments that enable it to interact with objects or individuals in the room 204. For example, the drone 282 may have landing gear that allow it to perch stably on the side of a crib, or it may have a hook or other system for retrieving, carrying, and releasing an object, such as a toy.

The drone 282 may have onboard electronics, such as a computer processor, that enable it to perform computing functions and operations. For example, the drone 282 may perform computing functions that enable it to navigate the room, avoid obstacles, identify objects of interest, or recognize individuals. The drone 282 may operate autonomously or under the influence of a remote operator, where the remote operator may be a computer system or a person.

The drone 282 may communicate with the monitoring system control unit 210 through the network 205. In some cases, the drone 282 may communicate wirelessly with the network 205, for instance, through WiFi, Bluetooth, or other means for wireless data transfer. The drone 282 may transmit data and other information to the control unit 210 through the network 205. For example, the drone 282 may send data collected by its onboard sensors to the control unit 210. The drone 282 may send unprocessed data, or the drone 282 send data that has been processed or partially processed by its onboard electronics.

The drone 282 may also receive commands or other data from the control unit 210. For example, the drone 282 may receive commands from the control unit 210 that direct it to move to a certain location, that regulate its onboard sensors, or that command it to perform an action, such as playing a recording.

In system 200, the control unit 210 configures the drone 282 to perform various actions to remotely monitor the baby 206. Here, the baby 206 is located within the room 204, while the parent 208 is located outside of the baby's room 204. The parent 208 may be in another room of the home or may be outside of the home (e.g., at work, at a restaurant) while another caretaker is present at the home.

In example (A), the control unit 210 configures the drone 282 to monitor the baby 206. In some implementations, baby monitoring requires that the drone 282 move to a location within the room 204 such that the baby 206 is in view of the drone's onboard camera. In example (A) of FIG. 2, the drone 282 is perched on the side of the crib with the drone's camera directed towards the baby 206. While monitoring the baby 206, the drone 282 sends video and audio data from its camera and microphone to the control unit 210 via the network 205.

As in system 100 of FIG. 1, the control unit 210 communicates with a monitoring server 260 that is remote from the home and which may be maintained and operated by a third-party monitoring company. The control unit 210 may send sensor data from the drone 282, as well as data from any other installed stationary sensors, to the monitoring server 260, which the monitoring server 260 may store, analyze, and synthesize, as described in the system 100.

The monitoring server 260 may then provide sensor or analyzed data to the parent 208 through the parent's mobile device 240. The monitoring server 260 may provide data to the mobile device 240 over a network, such as a cellular telephony network. In some implementations, the parent 208 may view and interact with the data through a software application on his mobile device 240. The parent 208 may also transmit information from his mobile device 240 to the monitor server 260.

As in system 100, in response to sensor data, analyzed data, and/or a command from the parent 208, the control unit 210 may direct the monitoring system to perform an action through any connected home automation controls.

In system 200, the drone 282 may also perform an action in response to a command from the parent 208. In example (B), the parent 208 has commanded the drone 282 to retrieve a dropped toy 209. Here, the parent 208 viewed on his mobile device 240 video data from a camera located on the drone 282 that revealed that a toy 209 had fallen onto the floor beside the baby's crib. The parent 208 sent a command from his mobile device 240 to the monitoring server 260 directing the drone 282 to retrieve the dropped toy 209 and place it into the baby's crib. The monitoring server 260 relayed the command to the control unit 210, which then sent the command to the drone 282 through the network 205.

In example (B), the drone 282 executes the operation by navigating to the dropped toy 209, picking up the toy 209, navigating to the baby's crib, and releasing the toy 209 in the crib next to the baby 206.

In some cases, the parent 208 may desire the drone 208 to remove an object from the baby's crib. For example, a younger baby may be placed at significantly increased risk for sudden infant death syndrome (SIDS) when they sleep beside blankets, stuffed animals, or other objects that may impede her breathing. In such a case, when the parent 208 observes an object in the crib that he determines to be too close to the baby 206, he may command the drone 208 to move the object further from the baby 206 or remove it from the baby's crib altogether.

In some implementations, the drone 282 may determine and execute the action automatically, without parental intervention. For instance, alternatively in example (B), the drone 282 may determine from video and/or audio data captured by its onboard camera and microphone that the baby 206 is crying. In response to determining that the baby 206 is crying, the drone 282 may be configured to visually scan the baby's room 204, identify the toy 209 on the floor, retrieve the toy 209, and place it in the crib next to the crying baby 206. As another example, the drone 208 may determine that a blanket in the crib is close enough to the baby 206 to present a potential breathing hazard and, in response to that determination, the drone 208 may automatically remove the blanket from the crib. In some implementations, the behavior of the drone 208 may change over time (i.e., transitioning from removing objects from the baby's crib to retrieving objects to the baby's crib) based on the age of the baby 206.

Similarly, the drone 282 may automatically perform other actions in response to sensor data and/or analyzed data. In example (C), the drone's onboard camera has detected that the light in the room exceeds a threshold level set by the parent 208. In response to the elevated light level, the drone 282 moves to the window and closes the window shade 216. The drone 282 may autonomously determine the action based on collected and/or analyzed data (e.g., using its onboard electronic computing resources to determine that the window shade 216 should be closed), or it may receive a command to perform the action from the control unit 210. In some cases, the action to be performed may be determined by the onboard computing resources of the drone 282. The action may also be determined by another computer within the home monitoring system 200, for example the control unit 210 or the monitoring server 260, and sent to the drone 282 over the network 205.

While FIG. 2 illustrates the drone 282 performing actions (A), (B), and (C) within the baby monitoring framework, these actions should be understood to be non-limiting examples of the many actions that a drone 282 might perform as part of a remote baby monitoring system. For example, the drone 282 may have an onboard speaker through which it broadcasts white noise, a lullaby, or other sounds to soothe the baby 206 when commanded. As another example, the drone 282 may produce a sound to rouse the baby 206 if she appears to be in distress. As another example, the drone 282 may display lights or images on its screen to entertain the baby 206. In some cases, the drone 282 may mechanically or electronically actuate other devices within room 204, such as a light switch.

In some implementations, a second mobile device, such as a smart phone or a tablet, may be substituted for the drone 282 to perform the monitoring function of example (A). When coupled with the communication pathway provided through the network 205, the control unit 210, and the monitoring server 260, the second mobile device paired with the parent's mobile device 240 provides an ad-hoc monitoring system that may be useful when no dedicated sensors or hardware are available. For example, the second mobile device may be equipped with an integrated camera and microphone. In some implementations, the second mobile device may be equipped with other sensors, for example a light sensor, temperature sensor, motion detector, or other sensor. The second mobile device is located within the baby's room 204 and in some implementations, may be situated such that the baby 206 is in view of the camera and microphone of the second mobile device. The second mobile device collects data through its sensors (e.g., video, audio, light level, or temperature data) that sense the condition of the room 204 and monitor the status of the baby 206. The second mobile device may send some or all of the data to the parent's mobile device 240. The second mobile device may also send processed data to the parent's mobile device 240. For example, the second mobile device may processes the collected video data to determine when the baby 206 is moving and send a notification to the parent's mobile device 240.

In some implementations, the second mobile device may send data to the control unit 210 through the network 205, which then sends the data to the parent's mobile device 240 through the monitoring server 260. The second mobile device may also send directly to the monitoring server 260 or to the parent's mobile device 240 through, for example, a cellular telephony network. The monitoring functions may be accomplished, for instance, through a software application stored in the second mobile device's memory and operable by the second mobile device's processor. In some implementations, the parent's mobile device 240 may also have a software application stored in its memory and operable by its processor that allows it to communicate with the second mobile device. In this way, the two mobile devices enable remote monitoring of the baby 206, even if the parents do not have dedicated stationary or mobile sensors in the baby's room 204.

Figure 3:
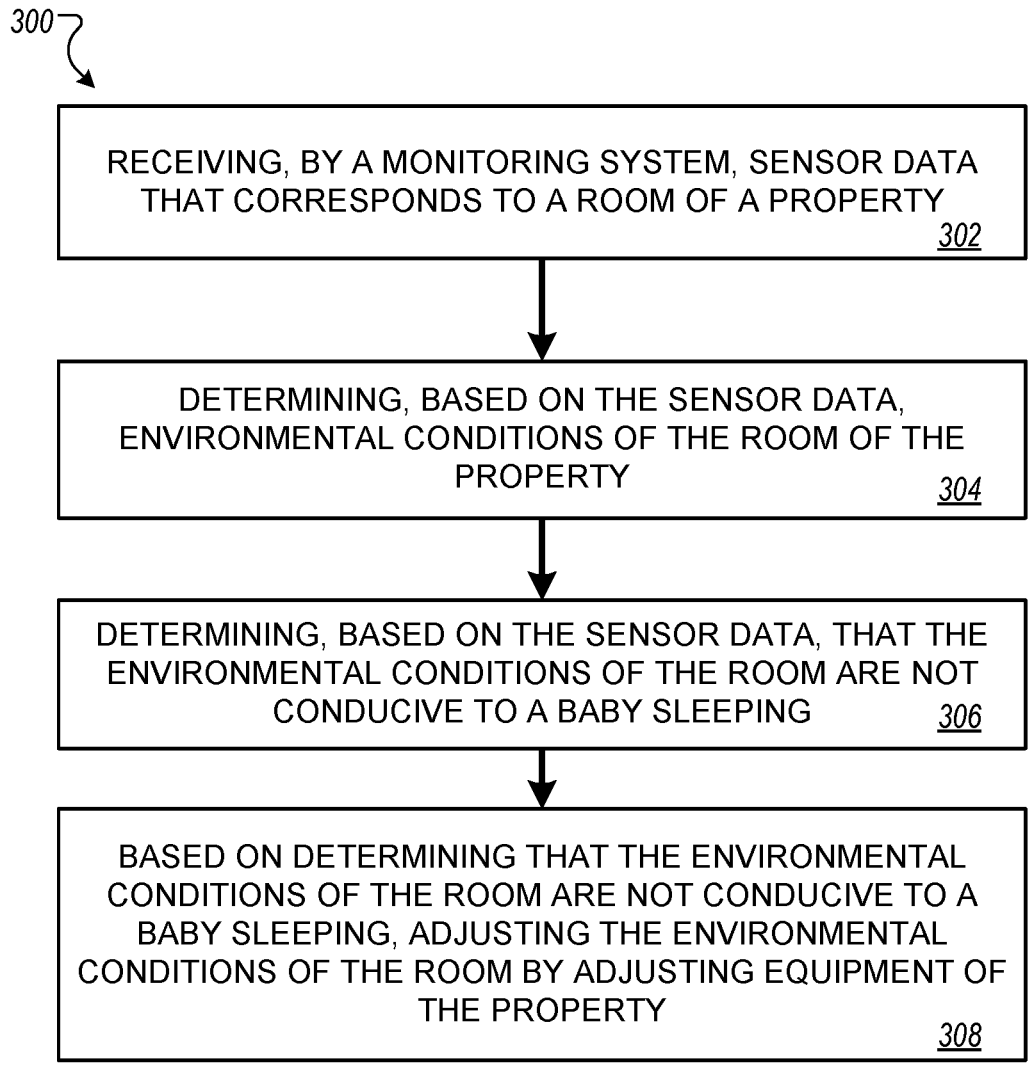
FIG. 3 is a flowchart illustrating an example method for remotely monitoring a baby using a home monitoring system.

FIG. 3 is a flowchart illustrating an example method 300 for remotely monitoring a baby using a home monitoring system. In method 300, the home monitoring system receives data from sensors installed in a baby's room on a property, determines the environmental conditions of the room and, based on determining that the environmental conditions of the room are not conducive to a baby sleeping, adjusts the environmental conditions of the room by adjusting equipment of the property.

In method 300, a home monitoring system receives sensor data that corresponds to a room of a property (302). The room may be, for instance, a baby's bedroom, a nursery, or another room on the property that the property owner desires to monitor. The sensor data may include data from cameras, microphones, motion detectors, mattress sensors or other sensors that are present in the room. The sensors data may also include data from temperature sensors, humidity sensors, light detectors, indoor air quality sensors, gas detectors, or other instruments that sense the environmental conditions within the room. The sensors that provide data may be integrated into the monitoring system platform. The sensors may also be separate from the monitoring system platform. For example, the home monitoring system may receive sensor data from a wearable health monitor attached to the baby. In some implementations, the sensor data may be collected, possibly through a wired or wireless network, by a control unit within the home monitoring system and located at the property. The control unit may send the sensor data to a monitoring server that is remote from the property, possibly through a wired or wireless network, for example, a wireless cellular telephony network, a cable connection, or a satellite link.

The home monitoring system determines, based on the sensor data, the environmental conditions of the room of the property (304). For example, the monitoring system may determine the temperature, the humidity, the light level, and/or air quality of the room.

The home monitoring system determines, based on the sensor data, that the environmental conditions of the room are not conducive to a baby sleeping (306). For example, based on the sensor data, the monitoring system may determine the sleep status of the baby in the room (e.g., awake and content, awake and crying, sleeping restlessly, sleeping restfully). When the baby is awake and crying or sleeping restlessly, the home monitoring system may determine that the environmental conditions of the room are not conducive to the baby sleeping. As another example, the parent or home monitoring system may have predetermined a preferred room temperature range conducive to the baby's safety or comfort. When the temperature of the room falls outside of that range, the home monitoring system may determine that the conditions of the room are not conducive to the sleep or safety of the baby.

In some implementations, the monitoring system may use sensor data to determine a baseline sleep pattern for the baby, where the baseline sleep pattern correlates the baby's sleep status with various factors (e.g., time of day, age, temperature, humidity, light level, etc.). The monitoring system may use the baseline sleep pattern to predict which environmental conditions are not conducive to the baby sleeping. For example, from the baseline sleep pattern, the monitoring system may predict that the baby does not sleep restfully when the temperature in the room is above 72° F.

The baseline sleep pattern may be determined, for example, by training a sleep model on historical sleep status data. The monitoring system may use data derived from different time periods to train a model or determine a baseline sleep pattern. For example, for young babies whose sleep habits change frequently, the monitoring system may determine a baseline sleep pattern based on two weeks of sleep data, while for older babies whose sleep habits are more established, the remote computer system may determine a baseline sleep pattern based on four or more weeks of sleep data. The monitoring system may determine a baseline sleep pattern that changes over time. For example, the monitoring system may determine a new baseline sleep pattern or update the existing baseline sleep pattern using the most recent sensor and sleep data available. Similarly, in some cases, the monitoring system may use the sensor data to determine a baseline waking activity pattern for the baby, where rather than tracking the baby's sleep status, the system tracks the baby's waking status (e.g., content, crying, agitated, etc.).

In some implementations, the monitoring system may also use data provided by the caregiver to determine the baseline sleep or activity pattern or train a sleep or activity model. For example, through an application on the caregiver's mobile device, the monitoring system may prompt the caregiver to indicate whether the baby is content or agitated at a given time. The monitoring system may use this, or other, information provided by the caregiver to train and refine the model.

The monitoring system may also perform other analytics on the sensor data. In some implementations, the monitoring system may analyze video and/or audio data to determine the position and orientation of the baby. For example, the monitoring system may determine that the baby is sleeping on her back, or sitting upright. In some cases, the monitoring system may also analyze sensor data to detect the baby's movement. For example, the monitoring system may determine the baby's breathing rate by detecting the rise and fall of the baby's chest or back. In some implementations, the monitoring system may analyze the baby's position, orientation, and movement to identify indications of the baby's well-being (e.g., regular breathing rate), distress (e.g., slowed or ceased breathing), or risk (e.g., baby's face is pressed against the side of the crib, baby is climbing the side of the crib).

In some cases, the monitoring system may store sensor data and/or analyzed data, including sleep data.

In some implementations, the monitoring system may provide sensor and analyzed data to a parent or caregiver. For example, the monitoring system may provide sensor and analyzed data to the parent's mobile device, where the mobile device is a smart phone, tablet, or other portable computing device. The monitoring system may send the data through a cellular telephony network, and the mobile device may receive the data through a software application stored in mobile device's memory and operable by the mobile device's processor. The software application may include a user interface that enables the parent to customize the data display and other features of the application. For example, the software application may allow the parent to view only the live video data from a camera in a baby's room or to silence the audio playback from a microphone in the baby's room. The parent may also choose to view data from environmental sensors within the baby's room (e.g., the temperature, humidity, light level, air quality), or he may choose to view historical sleep data for the baby that correlates sleep quality with environmental factors. In some cases, the software application may include a customizable dashboard that allows the parent to select which data sets are displayed.

In some implementations, the monitoring system may provide a notification to the parent through the parent's mobile device. For example, the monitoring system may send a notification to the parent's mobile device when it detects that the baby is in distress (e.g., slowed or ceased breathing) or that the conditions in the room represent an increased risk for the baby (e.g., the baby is sleeping on her stomach, the baby is climbing the side of the crib, the room temperature is above 72° F.). In some cases, the monitoring system may send a notification to the parent's mobile device when it detects that the baby has awoken, or when the temperature in the room is outside of a preferred range. In some cases, the software application may enable the parent to customize which notifications he receives. For example, the parent may choose to receive a notification that the baby is awake and crying, but he may choose not to receive a notification that the baby is awake and content.

Based on determining that the environmental conditions of the room are not conducive to a baby sleeping, the home monitoring system may adjust the environmental conditions of the room by adjusting equipment of the property (308). For example, the monitoring system may determine that the temperature in the room is outside of a preferred range determined to be conducive to a baby sleeping. Through an interconnected control, the home monitoring system may adjust the thermostat at the property to bring the temperature of the baby's room into the preferred temperature range.

In some implementations, the home monitoring system may adjust the conditions of the room in response to a command from the parent that is indicated through the parent's mobile device. For example, the parent may observe in the video data displayed in the software application on his mobile device that the baby is awake and crying. The parent may send, through the software application on his mobile device, a command to the monitoring system to turn on a sound machine in the baby's room. The monitoring system then turns on the sound machine through interconnected home automation controls.

In some implementations, the home monitoring system may automatically adjust the conditions of the room based on the received sensor data. For example, the monitoring system may detect that the baby's breathing is irregular and determine that the baby is in distress. In response to this determination, the monitoring system may automatically activate a vibrator on the baby's crib to attempt to rouse the baby. In some cases, the parent may configure the home monitoring system to adjust the conditions of the room based on various factors (e.g., sensor data, time of day, etc.).

Figure 4:
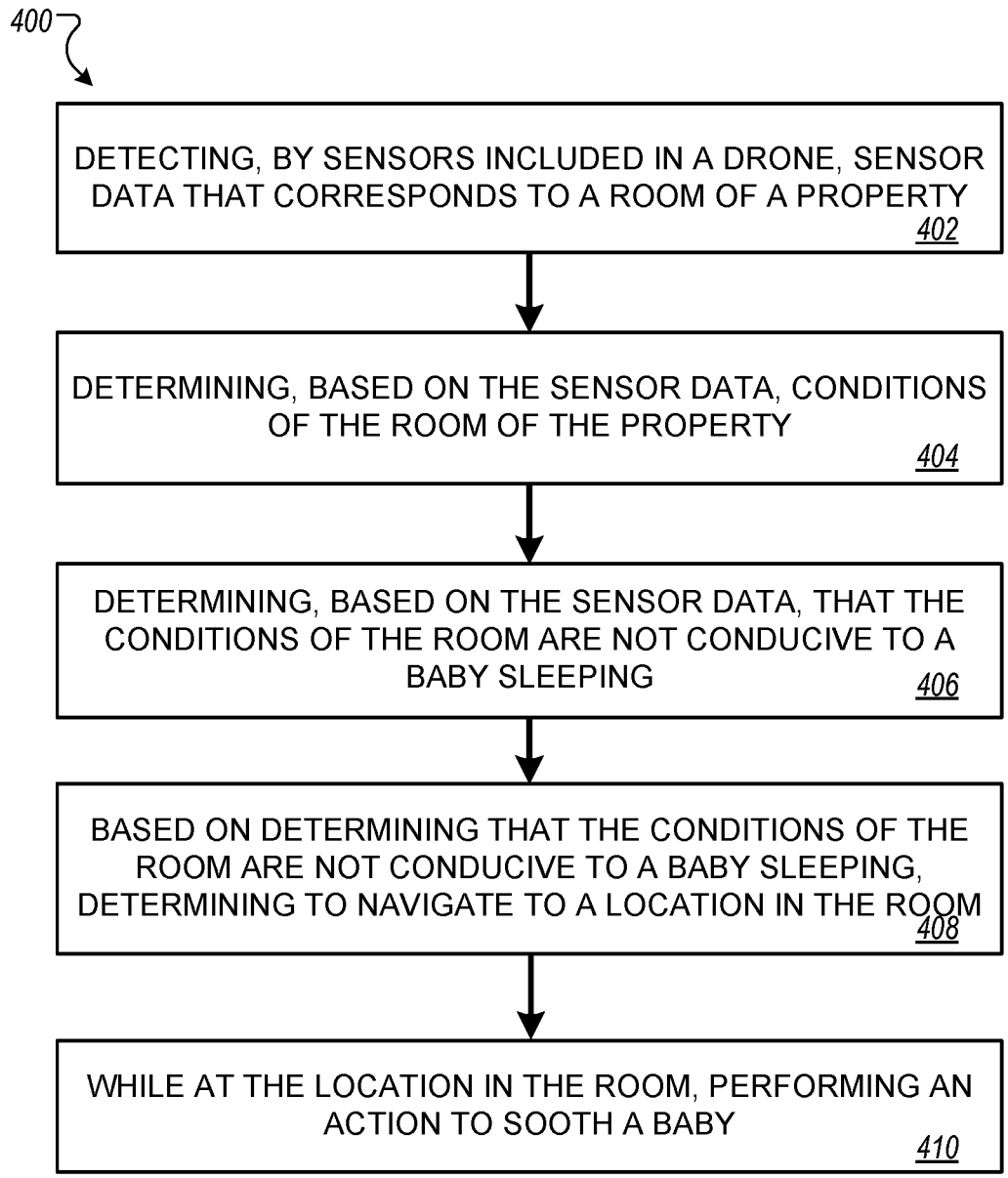
FIG. 4 is a flowchart illustrating an example method for remotely monitoring a baby using a home monitoring system that includes a mobile drone.

FIG. 4 is a flowchart illustrating an example method 400 for remotely monitoring a baby using a home monitoring system that includes a mobile drone. In method 400, a mobile drone located in a baby's room detects data from on-board sensors. Based on the sensor data, the drone determines that the environmental conditions in the room are not conducive to a baby sleeping, navigates to a location in the room, and, while at the location, performs an action to sooth the baby.

In method 400, a home monitoring system includes one or more drones that detect, by sensors included in the one or more drones, sensor data that corresponds to a room of a property (402). The room may be, for example, a baby's bedroom, a nursery, or another room on the property that the property owner desires to monitor. In some implementations, the drone may be an autonomous robot that can maneuver freely about the room. The drone may detect data from any of various sensors with which it is equipped. For example, the drone may be equipped with a camera, microphone, motion detector, or other sensor that provides information on the status of a baby present in the room. The drone may also be equipped with temperature sensors, humidity sensors, light detectors, indoor air quality sensors, gas detectors, or other sensors that provide information on the environmental conditions within the baby's room. The drone may position itself such that the baby is within view of the drone's camera and microphone, such that the captured video and audio data display the baby. In some implementations, the drone may transmit detected sensor data to a control unit within the home monitoring system, possibly through a wireless network. In some cases, the control unit may send the sensor data to a remote monitoring server over a wired or wireless network, for example, a wireless cellular telephony network, a cable connection, or a satellite link.

The mobile drone determines, based on the sensor data, conditions of the room of the property (404). For example, the drone may determine the temperature, the humidity, the light level, or air quality of the room. As another example, the drone may determine that a toy is on the floor of the room or that there is a blanket in the baby's crib.

Based on the sensor data, the mobile drone determines that the conditions of the room are not conducive to a baby sleeping (406). For example, based on the sensor data, the drone may determine the sleep status of the baby in the room (e.g., awake and content, awake and crying, sleeping restlessly, sleeping restfully). When the baby is awake and crying or sleeping restlessly, the drone may determine that the environmental conditions of the room are not conducive to the baby sleeping. For example, the blinds may be raised which lets too much light into the room. As another example, the drone may determine that the blanket in the baby's crib is too close to the baby, presenting a breathing hazard.

As in method 300, the drone or the monitoring system may use sensor data to determine a baseline sleep pattern for the baby, where the baseline sleep pattern may be determined by training a sleep model on historical sleep status data. The drone or monitoring system may use the baseline sleep pattern to predict which environmental conditions are not conducive to the baby sleeping. The drone or monitoring system may also perform other analytics on the sensor data. In some cases, the drone may determine that the environmental conditions of the room are not conducive to the baby sleeping based on data provided to it by the monitoring system.

As in method 300, in some implementations, the monitoring system may provide data to a parent or caregiver through a mobile device. The mobile device may receive data through a software application, where the software application may include a user interface to enable the parent to customize the data display and other application features. In some implementations, the monitoring system may provide notifications to the parent through the mobile device.

Based on determining that the conditions of the room are not conducive to a baby sleeping, the drone determines to navigate to a location in the room (408). For example, the drone may determine to navigate to a window, navigate towards the floor, or to perch on the side of the baby's crib.

While at the location in the room, the drone may perform an action to sooth the baby (410). For example, through an on-board camera or light detector, the drone may determine that the light level in the room is above a threshold level and is not conducive to a baby sleeping. The drone may navigate to a window within the room and lower the window shade to decrease the light level. As another example, the drone may determine that a blanket in the crib is too close to the baby. The drone may move to the crib and remove the blanket from the crib. In some implementations, the drone may navigate to a location in the room and/or perform an action in response to a command from the parent. For example, as in method 300, the parent may send a command to the home monitoring system through the software application on the parent's mobile device. The home monitoring system may relay the command to the drone, which then performs the commanded action.

The systems and methods described herein present several advantages compared to conventional techniques for baby monitoring. A parent can monitor and store a baby's sleep patterns over a period of days, weeks, or months, developing an historical record of sleep trends that can be used to track the baby's development, health, and overall well-being. By simultaneously monitoring the baby's sleep patterns and the condition of the baby's environment (e.g., temperature, humidity), the parent can determine the baby's preferred environment for sleep and modify the environment to enhance the baby's sleep quality. Parents can more easily determine whether ambient conditions, such as light level or type of noise machine, are conducive to the baby's restful sleep and thus modify the environment accordingly. The monitoring system can perform analytics that allow it to infer and predict environmental conditions that may disrupt a baby's sleep and notify a parent before the baby has awoken, giving the parent the opportunity to change the environment before the baby wakes. In some implementations, the parent can monitor a baby's waking activity patterns in addition to or instead of the baby's sleep patterns.

For example, the collected sensor data and analytics can track the baby's waken state (e.g., content, crying, agitated, etc.).

In some implementations, the monitoring system can alert a parent when a baby is in distress. For example, the monitoring system may analyze video data to determine a baby's breathing rate (e.g., by detecting the rise and fall of the baby's chest or back) and can alert a parent when the baby's breathing rate has slowed or stopped. Use of video analytics provides a non-invasive means for tracking a baby's breathing rate, an advantage over techniques that require connected sensors, which can disrupt the baby's sleep and may be sensitive to movement of the baby throughout the night. The monitoring system can also alert a parent to conditions that may present an increased danger or unsafe environment for the baby. For example, the risk of sudden infant death syndrome (SIDS) may considerably increase when the temperature in the baby's room is too warm or when the baby sleeps in certain orientations (e.g., on her stomach or side). The monitoring system can alert the parent when the room temperature rises above a predetermined value or when the baby is detected to be sleeping in an undesirable orientation, allowing the parent to address the condition if desired. The monitoring system can also notify a parent of other conditions in the room that present an unsafe or undesired environment for the baby, such as poor indoor air quality or too much light in the baby's room.

In some implementations, the parent can configure the monitoring system to automatically perform actions in response to a certain sensed condition or event. For example, the parent can configure the monitoring system to automatically turn on a noise machine when the system detects that the baby has awoken or automatically decrease the thermostat setting when the system detects that the baby's room temperature is above a preferred range. The parent can also configure the system to perform an action according to a schedule or on-demand. For example, the parent can configure the system to open a window shade at 3 PM each day when the baby should wake from her nap, or to turn on a sound machine when he sends a command through his mobile device.

The monitoring system can send sensor information or analyzed data to the parent's mobile device over a cellular telephony network, enabling the parent to remotely monitor the baby from almost anywhere, eliminating the requirement that the parent be within range of a monitoring terminal in order to receive updates. For example, parents out on a date can continue to monitor their baby while she is cared for by a babysitter at their home.

In some implementations, a drone present in the baby's room provides mobile sensors and controls that can monitor the baby, sense the environmental conditions, and perform actions. For example, a mobile drone may be equipped with a camera and microphone that can be moved to provide video images of the baby from different angles, improving motion detection. The drone may perform actions that enhance the baby's sleep or soothe the baby to sleep, including retrieving items that have fallen out of the baby's crib, moving a hazardous item out of a crib, playing a recording (e.g., a lullaby, white noise, recording of parent), or displaying an image on its screen. The drone can perform these actions without the parent having to enter the baby's room, reducing the disturbance to the baby and the parent.

In some implementations, the baby monitoring system utilizes sensors and communications equipment already installed as part of the home monitoring system, eliminating the need for additional dedicated hardware for remote baby monitoring. Sensor data may be collected by the monitoring system control unit, without requiring an additional data hub. Computationally intensive data processing and sleep analytics can be performed on a monitoring server remotely located from the home, requiring minimal logic and processing on local machines, which relaxes the requirements on the computer systems installed in the home monitoring system.

The baby monitoring system can be used to remotely monitor individuals other than babies. For example, the monitoring system may allow caregivers to monitor elderly persons, sick persons, pets, or other individuals in the home. The monitoring system can also be used by an individual to monitor their own sleep and activity patterns.

In some implementations, additional third party sensors can be integrated into the monitoring system, including wearable health devices that monitor the individual's heart rate, respiratory rate, glucose level, or other biometric markers. The additional sensor data can improve data analytics and model accuracy, as well as provide a caregiver with more extensive information regarding the correlation of his health status with his sleep/activity patterns and home environment conditions (e.g., temperature, humidity, air quality, etc.). In some cases, medical support devices, such as continuous positive airway pressure (CPAP) machines, may be integrated into the home monitoring system platform, where the devices may be monitored or controlled by the home monitoring system, providing the caregiver with additional data on sleep/activity patterns and alerting the caregiver of potentially dangerous device malfunctions.

Figure 5:
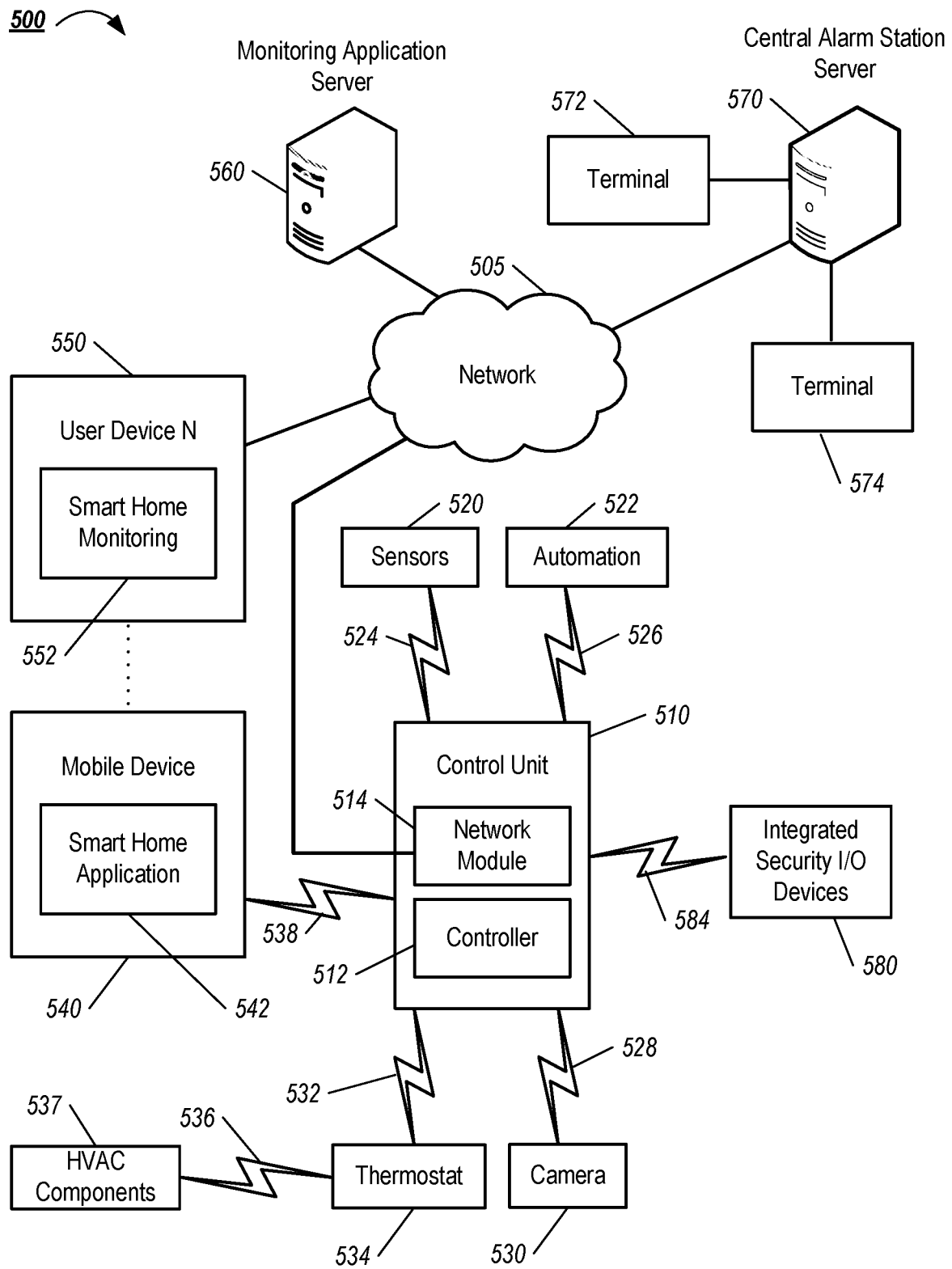
FIG. 5 is a block diagram illustrating an example home monitoring system.

FIG. 5 is a block diagram of an example home monitoring system 500. The electronic system 500 includes a network 505, a control unit 510, one or more user devices 540 and 550, a monitoring application server 560, and a central alarm station server 570. In some examples, the network 505 facilitates communications between the control unit 510, the one or more user devices 540 and 550, the monitoring application server 560, and the central alarm station server 570.

The network 505 is configured to enable exchange of electronic communications between devices connected to the network 505. For example, the network 505 may be configured to enable exchange of electronic communications between the control unit 510, the one or more user devices 540 and 550, the monitoring application server 560, and the central alarm station server 570. The network 505 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 505 may include multiple networks or subnetworks, each of which may include, for example, a wired or wireless data pathway. The network 505 may include a circuit-switched network, a packet-switched data network, or any other network able to carry electronic communications (e.g., data or voice communications). For example, the network 505 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 505 may include one or more networks that include wireless data channels and wireless voice channels. The network 505 may be a wireless network, a broadband network, or a combination of networks including a wireless network and a broadband network.

The control unit 510 includes a controller 512 and a network module 514. The controller 512 is configured to control a control unit monitoring system (e.g., a control unit system) that includes the control unit 510. In some examples, the controller 512 may include a processor or other control circuitry configured to execute instructions of a program that controls operation of a control unit system. In these examples, the controller 512 may be configured to receive input from sensors, flow meters, or other devices included in the control unit system and control operations of devices included in the household (e.g., speakers, lights, doors, etc.). For example, the controller 512 may be configured to control operation of the network module 514 included in the control unit 510.

The network module 514 is a communication device configured to exchange communications over the network 505. The network module 514 may be a wireless communication module configured to exchange wireless communications over the network 505. For example, the network module 514 may be a wireless communication device configured to exchange communications over a wireless data channel and a wireless voice channel. In this example, the network module 514 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 514 also may be a wired communication module configured to exchange communications over the network 505 using a wired connection. For instance, the network module 514 may be a modem, a network interface card, or another type of network interface device. The network module 514 may be an Ethernet network card configured to enable the control unit 510 to communicate over a local area network and/or the Internet. The network module 514 also may be a voiceband modem configured to enable the alarm panel to communicate over the telephone lines of Plain Old Telephone Systems (POTS).

The control unit system that includes the control unit 510 includes one or more sensors. For example, the monitoring system may include multiple sensors 520. The sensors 520 may include a lock sensor, a contact sensor, a motion sensor, or any other type of sensor included in a control unit system. The sensors 520 also may include an environmental sensor, such as a temperature sensor, a water sensor, a rain sensor, a wind sensor, a light sensor, a smoke detector, a carbon monoxide detector, an air quality sensor, etc. The sensors 520 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the sensors 520 may include a radio-frequency identification (RFID) sensor that identifies a particular article that includes a pre-assigned RFID tag.

The control unit 510 communicates with the module 522 and the camera 530 to perform monitoring. The module 522 is connected to one or more devices that enable home automation control. For instance, the module 522 may be connected to one or more lighting systems and may be configured to control operation of the one or more lighting systems. Also, the module 522 may be connected to one or more electronic locks at the property and may be configured to control operation of the one or more electronic locks (e.g., control Z-Wave locks using wireless communications in the Z-Wave protocol. Further, the module 522 may be connected to one or more appliances at the property and may be configured to control operation of the one or more appliances. The module 522 may include multiple modules that are each specific to the type of device being controlled in an automated manner. The module 522 may control the one or more devices based on commands received from the control unit 510. For instance, the module 522 may cause a lighting system to illuminate an area to provide a better image of the area when captured by a camera 530.

The camera 530 may be a video/photographic camera or other type of optical sensing device configured to capture images. For instance, the camera 530 may be configured to capture images of an area within a building or within a residential facility 102-A monitored by the control unit 510. The camera 530 may be configured to capture single, static images of the area and also video images of the area in which multiple images of the area are captured at a relatively high frequency (e.g., thirty images per second). The camera 530 may be controlled based on commands received from the control unit 510.

The camera 530 may be triggered by several different types of techniques. For instance, a Passive Infra-Red (PIR) motion sensor may be built into the camera 530 and used to trigger the camera 530 to capture one or more images when motion is detected. The camera 530 also may include a microwave motion sensor built into the camera and used to trigger the camera 530 to capture one or more images when motion is detected. The camera 530 may have a "normally open" or "normally closed" digital input that can trigger capture of one or more images when external sensors (e.g., the sensors 520, PIR, door/window, etc.) detect motion or other events. In some implementations, the camera 530 receives a command to capture an image when external devices detect motion or another potential alarm event. The camera 530 may receive the command from the controller 512 or directly from one of the sensors 520.

In some examples, the camera 530 triggers integrated or external illuminators (e.g., Infra-Red, Z-wave controlled "white" lights, lights controlled by the module 522, etc.) to improve image quality when the scene is dark. An integrated or separate light sensor may be used to determine if illumination is desired and may result in increased image quality.

The camera 530 may be programmed with any combination of time/day schedules, system "arming state", or other variables to determine whether images should be captured or not when triggers occur. The camera 530 may enter a low-power mode when not capturing images. In this case, the camera 530 may wake periodically to check for inbound messages from the controller 512. The camera 530 may be powered by internal, replaceable batteries if located remotely from the control unit 510. The camera 530 may employ a small solar cell to recharge the battery when light is available. Alternatively, the camera 530 may be powered by the controller's 512 power supply if the camera 530 is co-located with the controller 512.

In some implementations, the camera 530 communicates directly with the monitoring application server 560 over the Internet. In these implementations, image data captured by the camera 530 does not pass through the control unit 510 and the camera 530 receives commands related to operation from the monitoring application server 560.

The system 500 also includes thermostat 534 to perform dynamic environmental control at the property. The thermostat 534 is configured to monitor temperature and/or energy consumption of an HVAC system associated with the thermostat 534, and is further configured to provide control of environmental (e.g., temperature) settings. In some implementations, the thermostat 534 can additionally or alternatively receive data relating to activity at a property and/or environmental data at a property, e.g., at various locations indoors and outdoors at the property. The thermostat 534 can directly measure energy consumption of the HVAC system associated with the thermostat, or can estimate energy consumption of the HVAC system associated with the thermostat 534, for example, based on detected usage of one or more components of the HVAC system associated with the thermostat 534. The thermostat 534 can communicate temperature and/or energy monitoring information to or from the control unit 510 and can control the environmental (e.g., temperature) settings based on commands received from the control unit 510.

In some implementations, the thermostat 534 is a dynamically programmable thermostat and can be integrated with the control unit 510. For example, the dynamically programmable thermostat 534 can include the control unit 510, e.g., as an internal component to the dynamically programmable thermostat 534. In addition, the control unit 510 can be a gateway device that communicates with the dynamically programmable thermostat 534.

A module 537 is connected to one or more components of an HVAC system associated with a property, and is configured to control operation of the one or more components of the HVAC system. In some implementations, the module 537 is also configured to monitor energy consumption of the HVAC system components, for example, by directly measuring the energy consumption of the HVAC system components or by estimating the energy usage of the one or more HVAC system components based on detecting usage of components of the HVAC system. The module 537 can communicate energy monitoring information and the state of the HVAC system components to the thermostat 534 and can control the one or more components of the HVAC system based on commands received from the thermostat 534.

In some examples, the system 500 further includes one or more robotic devices. The robotic devices may be any type of robots that are capable of moving and taking actions that assist in security monitoring. For example, the robotic devices may include drones that are capable of moving throughout a property based on automated control technology and/or user input control provided by a user. In this example, the drones may be able to fly, roll, walk, or otherwise move about the property. The drones may include helicopter type devices (e.g., quad copters), rolling helicopter type devices (e.g., roller copter devices that can fly and also roll along the ground, walls, or ceiling) and land vehicle type devices (e.g., automated cars that drive around a property). In some cases, the robotic devices may be robotic devices that are intended for other purposes and merely associated with the system 500 for use in appropriate circumstances. For instance, a robotic vacuum cleaner device may be associated with the monitoring system 500 as one of the robotic devices and may be controlled to take action responsive to monitoring system events.

In some examples, the robotic devices automatically navigate within a property. In these examples, the robotic devices include sensors and control processors that guide movement of the robotic devices within the property. For instance, the robotic devices may navigate within the property using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices may include control processors that process output from the various sensors and control the robotic devices to move along a path that reaches the desired destination and avoids obstacles. In this regard, the control processors detect walls or other obstacles in the property and guide movement of the robotic devices in a manner that avoids the walls and other obstacles.

In addition, the robotic devices may store data that describes attributes of the property. For instance, the robotic devices may store a floorplan and/or a three-dimensional model of the property that enables the robotic devices to navigate the property. During initial configuration, the robotic devices may receive the data describing attributes of the property, determine a frame of reference to the data (e.g., a home or reference location in the property), and navigate the property based on the frame of reference and the data describing attributes of the property. Further, initial configuration of the robotic devices also may include learning of one or more navigation patterns in which a user provides input to control the robotic devices to perform a specific navigation action (e.g., fly to an upstairs bedroom and spin around while capturing video and then return to a home charging base). In this regard, the robotic devices may learn and store the navigation patterns such that the robotic devices may automatically repeat the specific navigation actions upon a later request.

In some examples, the robotic devices may include data capture and recording devices. In these examples, the robotic devices may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the property and users in the property. The one or more biometric data collection tools may be configured to collect biometric samples of a person in the home with or without contact of the person. For instance, the biometric data collection tools may include a fingerprint scanner, a hair sample collection tool, a skin cell collection tool, and/or any other tool that allows the robotic devices to take and store a biometric sample that can be used to identify the person (e.g., a biometric sample with DNA that can be used for DNA testing).

In some implementations, the robotic devices may include output devices. In these implementations, the robotic devices may include one or more displays, one or more speakers, and/or any type of output devices that allow the robotic devices to communicate information to a nearby user.

The robotic devices also may include a communication module that enables the robotic devices to communicate with the control unit 510, each other, and/or other devices. The communication module may be a wireless communication module that allows the robotic devices to communicate wirelessly. For instance, the communication module may be a Wi-Fi module that enables the robotic devices to communicate over a local wireless network at the property. The communication module further may be a 900 MHz wireless communication module that enables the robotic devices to communicate directly with the control unit 510.

Other types of short-range wireless communication protocols, such as Bluetooth, Bluetooth LE, Zwave, Zigbee, etc., may be used to allow the robotic devices to communicate with other devices in the property.

The robotic devices further may include processor and storage capabilities. The robotic devices may include any suitable processing devices that enable the robotic devices to operate applications and perform the actions described throughout this disclosure. In addition, the robotic devices may include solid state electronic storage that enables the robotic devices to store applications, configuration data, collected sensor data, and/or any other type of information available to the robotic devices.

The robotic devices are associated with one or more charging stations. The charging stations may be located at predefined home base or reference locations in the property. The robotic devices may be configured to navigate to the charging stations after completion of tasks needed to be performed for the monitoring system 500. For instance, after completion of a monitoring operation or upon instruction by the control unit 510, the robotic devices may be configured to automatically fly to and land on one of the charging stations. In this regard, the robotic devices may automatically maintain a fully charged battery in a state in which the robotic devices are ready for use by the monitoring system 500.

The charging stations may be contact based charging stations and/or wireless charging stations. For contact based charging stations, the robotic devices may have readily accessible points of contact that the robotic devices are capable of positioning and mating with a corresponding contact on the charging station. For instance, a helicopter type robotic device may have an electronic contact on a portion of its landing gear that rests on and mates with an electronic pad of a charging station when the helicopter type robotic device lands on the charging station. The electronic contact on the robotic device may include a cover that opens to expose the electronic contact when the robotic device is charging and closes to cover and insulate the electronic contact when the robotic device is in operation.

For wireless charging stations, the robotic devices may charge through a wireless exchange of power. In these cases, the robotic devices need only locate themselves closely enough to the wireless charging stations for the wireless exchange of power to occur. In this regard, the positioning needed to land at a predefined home base or reference location in the property may be less precise than with a contact based charging station. Based on the robotic devices landing at a wireless charging station, the wireless charging station outputs a wireless signal that the robotic devices receive and convert to a power signal that charges a battery maintained on the robotic devices.

In some implementations, each of the robotic devices has a corresponding and assigned charging station such that the number of robotic devices equals the number of charging stations. In these implementations, the robotic devices always navigate to the specific charging station assigned to that robotic device. For instance, a first robotic device may always use a first charging station and a second robotic device may always use a second charging station.

In some examples, the robotic devices may share charging stations. For instance, the robotic devices may use one or more community charging stations that are capable of charging multiple robotic devices. The community charging station may be configured to charge multiple robotic devices in parallel. The community charging station may be configured to charge multiple robotic devices in serial such that the multiple robotic devices take turns charging and, when fully charged, return to a predefined home base or reference location in the property that is not associated with a charger. The number of community charging stations may be less than the number of robotic devices.

Also, the charging stations may not be assigned to specific robotic devices and may be capable of charging any of the robotic devices. In this regard, the robotic devices may use any suitable, unoccupied charging station when not in use. For instance, when one of the robotic devices has completed an operation or is in need of battery charge, the control unit 510 references a stored table of the occupancy status of each charging station and instructs the robotic device to navigate to the nearest charging station that is unoccupied.

The system 500 further includes one or more integrated security devices 580. The one or more integrated security devices may include any type of device used to provide alerts based on received sensor data. For instance, the one or more control units 510 may provide one or more alerts to the one or more integrated security input/output devices. Additionally, the one or more control units 510 may receive one or more sensor data from the sensors 520 and determine whether to provide an alert to the one or more integrated security input/output devices 580.

The sensors 520, the module 522, the camera 530, the thermostat 534, and the integrated security devices 580 communicate with the controller 512 over communication links 524, 526, 528, 532, 584, and 586. The communication links 524, 526, 528, 532, 584, and 586 may be a wired or wireless data pathway configured to transmit signals from the sensors 520, the module 522, the camera 530, the thermostat 534, and the integrated security devices 580 to the controller 512. The sensors 520, the module 522, the camera 530, the thermostat 534, and the integrated security devices 580 may continuously transmit sensed values to the controller 512, periodically transmit sensed values to the controller 512, or transmit sensed values to the controller 512 in response to a change in a sensed value.

The communication links 524, 526, 528, 532, 584, and 586 may include a local network. The sensors 520, the module 522, the camera 530, the thermostat 534, and the integrated security devices 580, and the controller 512 may exchange data and commands over the local network. The local network may include 802.11 "Wi-Fi" wireless Ethernet (e.g., using low-power Wi-Fi chipsets), Z-Wave, Zigbee, Bluetooth, "Homeplug" or other "Powerline" networks that operate over AC wiring, and a Category 5 (CAT5) or Category 5 (CAT6) wired Ethernet network. The local network may be a mesh network constructed based on the devices connected to the mesh network.

The monitoring application server 560 is an electronic device configured to provide monitoring services by exchanging electronic communications with the control unit 510, the one or more user devices 540 and 550, and the central alarm station server 570 over the network 505. For example, the monitoring application server 560 may be configured to monitor events (e.g., alarm events) generated by the control unit 610. In this example, the monitoring application server 660 may exchange electronic communications with the network module 514 included in the control unit 510 to receive information regarding events (e.g., alerts) detected by the control unit server 104a. The monitoring application server 560 also may receive information regarding events (e.g., alerts) from the one or more user devices 540 and 550.

In some examples, the monitoring application server 560 may route alert data received from the network module 514 or the one or more user devices 540 and 550 to the central alarm station server 570. For example, the monitoring application server 560 may transmit the alert data to the central alarm station server 570 over the network 505.

The monitoring application server 560 may store sensor and image data received from the monitoring system and perform analysis of sensor and image data received from the monitoring system. Based on the analysis, the monitoring application server 560 may communicate with and control aspects of the control unit 510 or the one or more user devices 540 and 550.

The central alarm station server 570 is an electronic device configured to provide alarm monitoring service by exchanging communications with the control unit 510, the one or more mobile devices 540 and 550, and the monitoring application server 560 over the network 505. For example, the central alarm station server 570 may be configured to monitor alerting events generated by the control unit 510. In this example, the central alarm station server 570 may exchange communications with the network module 514 included in the control unit 510 to receive information regarding alerting events detected by the control unit 510. The central alarm station server 570 also may receive information regarding alerting events from the one or more mobile devices 540 and 550 and/or the monitoring application server 560.

The central alarm station server 570 is connected to multiple terminals 572 and 574. The terminals 572 and 574 may be used by operators to process alerting events. For example, the central alarm station server 570 may route alerting data to the terminals 572 and 574 to enable an operator to process the alerting data. The terminals 572 and 574 may include general-purpose computers (e.g., desktop personal computers, workstations, or laptop computers) that are configured to receive alerting data from a server in the central alarm station server 570 and render a display of information based on the alerting data. For instance, the controller 512 may control the network module 514 to transmit, to the central alarm station server 570, alerting data indicating that a sensor 520 detected motion from a motion sensor via the sensors 520. The central alarm station server 570 may receive the alerting data and route the alerting data to the terminal 572 for processing by an operator associated with the terminal 572. The terminal 572 may render a display to the operator that includes information associated with the alerting event (e.g., the lock sensor data, the motion sensor data, the contact sensor data, etc.) and the operator may handle the alerting event based on the displayed information.

In some implementations, the terminals 572 and 574 may be mobile devices or devices designed for a specific function. Although FIG. 6 illustrates two terminals for brevity, actual implementations may include more (and, perhaps, many more) terminals.

The one or more user devices 540 and 550 are devices that host and display user interfaces. For instance, the user device 540 is a mobile device that hosts one or more native applications (e.g., the smart home application 542). The user device 540 may be a cellular phone or a non-cellular locally networked device with a display. The user device 540 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 540 may perform functions unrelated to the monitoring system, such as placing personal telephone calls, playing music, playing video, displaying pictures, browsing the Internet, maintaining an electronic calendar, etc.

The user device 540 includes a smart home application 542. The smart home application 542 refers to a software/firmware program running on the corresponding mobile device that enables the user interface and features described throughout. The user device 540 may load or install the smart home application 542 based on data received over a network or data received from local media. The smart home application 542 runs on mobile devices platforms, such as iPhone, iPod touch, Blackberry, Google Android, Windows Mobile, etc. The smart home application 542 enables the user device 540 to receive and process image and sensor data from the monitoring system.

The user device 550 may be a general-purpose computer (e.g., a desktop personal computer, a workstation, or a laptop computer) that is configured to communicate with the monitoring application server 560 and/or the control unit 510 over the network 505. The user device 550 may be configured to display a smart home user interface 552 that is generated by the user device 550 or generated by the monitoring application server 560. For example, the user device 550 may be configured to display a user interface (e.g., a web page) provided by the monitoring application server 560 that enables a user to perceive images captured by the camera 530 and/or reports related to the monitoring system. Although FIG. 6 illustrates two user devices for brevity, actual implementations may include more (and, perhaps, many more) or fewer user devices.

In some implementations, the one or more user devices 540 and 550 communicate with and receive monitoring system data from the control unit 510 using the communication link 538. For instance, the one or more user devices 540 and 550 may communicate with the control unit 510 using various local wireless protocols such as Wi-Fi, Bluetooth, Zwave, Zigbee, HomePlug (ethernet over powerline), or wired protocols such as Ethernet and USB, to connect the one or more user devices 540 and 550 to local security and automation equipment. The one or more user devices 540 and 550 may connect locally to the monitoring system and its sensors and other devices. The local connection may improve the speed of status and control communications because communicating through the network 505 with a remote server (e.g., the monitoring application server 560) may be significantly slower.

Although the one or more user devices 540 and 550 are shown as communicating with the control unit 510, the one or more user devices 540 and 550 may communicate directly with the sensors and other devices controlled by the control unit 510. In some implementations, the one or more user devices 540 and 550 replace the control unit 510 and perform the functions of the control unit 510 for local monitoring and long range/offsite communication.

In other implementations, the one or more user devices 540 and 550 receive monitoring system data captured by the control unit 510 through the network 505. The one or more user devices 540, 550 may receive the data from the control unit 510 through the network 505 or the monitoring application server 560 may relay data received from the control unit 510 to the one or more user devices 540 and 550 through the network 505. In this regard, the monitoring application server 560 may facilitate communication between the one or more user devices 540 and 550 and the monitoring system.

In some implementations, the one or more user devices 540 and 550 may be configured to switch whether the one or more user devices 540 and 550 communicate with the control unit 510 directly (e.g., through link 538) or through the monitoring application server 560 (e.g., through network 505) based on a location of the one or more user devices 540 and 550. For instance, when the one or more user devices 540 and 550 are located close to the control unit 510 and in range to communicate directly with the control unit 510, the one or more user devices 540 and 550 use direct communication. When the one or more user devices 540 and 550 are located far from the control unit 510 and not in range to communicate directly with the control unit 510, the one or more user devices 540 and 550 use communication through the monitoring application server 560.

Although the one or more user devices 540 and 550 are shown as being connected to the network 505, in some implementations, the one or more user devices 540 and 550 are not connected to the network 505. In these implementations, the one or more user devices 540 and 550 communicate directly with one or more of the monitoring system components and no network (e.g., Internet) connection or reliance on remote servers is needed.

In some implementations, the one or more user devices 540 and 550 are used in conjunction with only local sensors and/or local devices in a house. In these implementations, the system 500 only includes the one or more user devices 540 and 550, the sensors 520, the module 522, the camera 530, and the robotic devices. The one or more user devices 540 and 550 receive data directly from the sensors 520, the module 522, the camera 530, and the robotic devices and sends data directly to the sensors 520, the module 522, the camera 530, and the robotic devices. The one or more user devices 540, 550 provide the appropriate interfaces/processing to provide visual surveillance and reporting.

In other implementations, the system 500 further includes network 505 and the sensors 520, the module 522, the camera 530, the thermostat 534, and the robotic devices are configured to communicate sensor and image data to the one or more user devices 540 and 550 over network 505 (e.g., the Internet, cellular network, etc.). In yet another implementation, the sensors 520, the module 522, the camera 530, the thermostat 534, and the robotic devices (or a component, such as a bridge/router) are intelligent enough to change the communication pathway from a direct local pathway when the one or more user devices 540 and 550 are in close physical proximity to the sensors 520, the module 522, the camera 530, the thermostat 534, and the robotic devices to a pathway over network 505 when the one or more user devices 540 and 550 are farther from the sensors 520, the module 522, the camera 530, the thermostat 534, and the robotic devices. In some examples, the system leverages GPS information from the one or more user devices 540 and 550 to determine whether the one or more user devices 540 and 550 are close enough to the sensors 520, the module 522, the camera 530, the thermostat 534, and the robotic devices to use the direct local pathway or whether the one or more user devices 540 and 550 are far enough from the sensors 520, the module 522, the camera 530, the thermostat 534, and the robotic devices that the pathway over network 505 is required. In other examples, the system leverages status communications (e.g., pinging) between the one or more user devices 540 and 550 and the sensors 520, the module 522, the camera 530, the thermostat 534, and the robotic devices to determine whether communication using the direct local pathway is possible. If communication using the direct local pathway is possible, the one or more user devices 540 and 550 communicate with the sensors 520, the module 522, the camera 530, the thermostat 534, and the robotic devices using the direct local pathway. If communication using the direct local pathway is not possible, the one or more user devices 540 and 550 communicate with the sensors 520, the module 522, the camera 530, the thermostat 534, and the robotic devices using the pathway over network 505.

In some implementations, the system 500 provides end users with access to images captured by the camera 530 to aid in decision making. The system 500 may transmit the images captured by the camera 530 over a wireless WAN network to the user devices 540 and 550. Because transmission over a wireless WAN network may be relatively expensive, the system 500 uses several techniques to reduce costs while providing access to significant levels of useful visual information.

In some implementations, a state of the monitoring system and other events sensed by the monitoring system may be used to enable/disable video/image recording devices (e.g., the camera 530). In these implementations, the camera 530 may be set to capture images on a periodic basis when the alarm system is armed in an "Away" state, but set not to capture images when the alarm system is armed in a "Stay" state or disarmed. In addition, the camera 530 may be triggered to begin capturing images when the alarm system detects an event, such as an alarm event, a door-opening event for a door that leads to an area within a field of view of the camera 530, or motion in the area within the field of view of the camera 530. In other implementations, the camera 530 may capture images continuously, but the captured images may be stored or transmitted over a network when needed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A monitoring system that is configured to monitor a property, the monitoring system comprising:
   a sensor that is located in a room of the property and that is configured to generate sensor data; and
   a monitor control unit that is configured to:
      receive the sensor data;
      based on the sensor data, determine environmental conditions of the room;
      determine whether the environmental conditions of the room are conducive to a baby sleeping; and
      based on determining whether the environmental conditions of the room are conducive to a baby sleeping, perform a monitoring system action,
   wherein the monitor control unit is configured to perform the monitoring system action by instructing a drone to perform an action directed to adjusting the environmental conditions of the room by at least one of:
   instructing the drone to adjust a position of a window covering in the room,
   instructing the drone to rock a cradle of the baby, or
   instructing the drone to retrieve a toy and place the toy in the cradle of the baby.

2. The monitoring system of claim 1, wherein the monitor control unit is configured to:
   perform a monitoring system action by storing data indicating a temperature setting of the room, a position of a window covering in the room, a time of day, and a volume level of a noise machine in the room.

3. The monitoring system of claim 1, wherein the monitor control unit is configured to:
   perform a monitoring system action by adjusting a temperature setting of the room and adjusting a volume level of a noise machine in the room.

4. The monitoring system of claim 3, wherein:
   the drone includes the noise machine, and
   the monitor control unit is configured to:
      adjusting the volume level of the noise machine in the room by instructing the drone to adjust the volume level of the noise machine included in the drone.

5. The monitoring system of claim 1, wherein the monitor control unit is configured to:
   adjust the position of the window covering in the room by instructing the drone to adjust the position of the window covering in the room.

6. The monitoring system of claim 1, wherein:
   the sensor is a light sensor that is configured to generate sensor data indicating a light level in the room.

7. The monitoring system of claim 1, wherein:
   the sensor is a microphone that is configured to receive audio data in the room.

8. The monitoring system of claim 1, wherein:
   the sensor is a camera that is configured to generate image data that includes a representation of the room.

9. The monitoring system of claim 1, wherein:
   the sensor is a thermometer that is configured to generate temperature data that indicates a temperature of the room.

10. The monitoring system of claim 1, wherein:
    the sensor is a humidity sensor that is configured to generate humidity data that indicates a humidity level in the room.

11. The monitoring system of claim 1, wherein:
    the sensor is an air quality sensor that is configured to generate air quality data that indicates an air quality level in the room.

12. The monitoring system of claim 1, wherein:
    the sensor is an audio-visual camera that is configured to generate image data that includes a representation of the room and that is configured to receive audio data in the room, and
    the monitor control unit is configured to:
       receive the sensor data by receiving the image data and the audio data;
       based on the image data, determine that a baby is in the room;
       based on the audio data, determine that the baby is crying; and
       perform the monitoring system action based on determining that the baby is in the room and that the baby is crying.

13. The monitoring system of claim 12, wherein the monitor control unit is configured to:
    perform the monitoring system action by instructing the drone to rock the cradle of the baby.

14. The monitoring system of claim 12, wherein the monitor control unit is configured to:
    based on the image data, determine that the toy of the baby is not within a threshold distance of the baby; and
    perform the monitoring system action by instructing the drone to retrieve the toy and place the toy in the cradle of the baby.

15. The monitoring system of claim 1, wherein:
    the sensor is an audio-visual camera that is configured to generate image data that includes a representation of the room and that is configured to receive audio data in the room, and
    the monitor control unit is configured to:
       receive the sensor data by receiving the image data and the audio data;
       based on the image data, determine that a baby is in the room;
       based on the audio data, determine that the baby is not crying; and
       store data indicating current environmental conditions of the room as environmental conditions of the room that are conducive to a baby sleeping.

16. A computer-implemented method, comprising:
    receiving, from a sensor that is located in a room of a property and that is included in a monitoring system that is configured to monitor the property, sensor data;
    based on the sensor, determining, by the monitoring system, environmental conditions of the room;
    determining, by the monitoring system, whether the environmental conditions of the room are conducive to a baby sleeping; and
    based on determining whether the environmental conditions of the room are conducive to a baby sleeping, performing, by the monitoring system, a monitoring system action, wherein performing the monitoring system action comprises instructing a drone to perform an action directed to adjusting the environmental conditions of the room by at least one of:

instructing the drone to adjust a position of a window covering in the room, instructing the drone to rock a cradle of the baby, or instructing the drone to retrieve a toy and place the toy in the cradle of the baby.

17. The method of claim 16, comprising:

performing a monitoring system action by storing data indicating a temperature setting of the room, a position of a window covering in the room, a time of day, and a volume level of a noise machine in the room.

18. The method of claim 16, comprising:

performing a monitoring system action by adjusting a temperature setting of the room and adjusting a volume level of a noise machine in the room.

19. The method of claim 16, wherein:

the sensor is a light sensor that is configured to generate sensor data indicating a light level in the room, the sensor is a microphone that is configured to receive audio data in the room, the sensor is a camera that is configured to generate image data that includes a representation of the room, the sensor is a thermometer that is configured to generate temperature data that indicates a temperature of the room, the sensor is a humidity sensor that is configured to generate humidity data that indicates a humidity level in the room, or the sensor is an air quality sensor that is configured to generate air quality data that indicates an air quality level in the room.

20. The method of claim 16, wherein:

the sensor is an audio-visual camera that is configured to generate image data that includes a representation of the room and that is configured to receive audio data in the room, and the method comprises:

receiving the sensor data by receiving the image data and the audio data;

based on the image data, determining that a baby is in the room;

based on the audio data, determining that the baby is crying; and performing the monitoring system action based on determining that the baby is in the room and that the baby is crying.

* * * * *